United States Patent [19]
Bolton et al.

[11] Patent Number: 5,763,577
[45] Date of Patent: Jun. 9, 1998

[54] SUBSTITUTED TETRA- AND PENTAPEPTIDE INHIBITORS OF PROTEIN: FARNESYL TRANSFERASE

[75] Inventors: Gary Louis Bolton, Ann Arbor, Mich.; Alfred Campbell, Wilmette, Ill.; Richard Gowan, Plymouth, Mich.; John Cooke Hodges, Ann Arbor, Mich.; Donald Hupe, Ann Arbor, Mich.; Daniele Leonard, Ann Arbor, Mich.; Tomi Sawyer, Ann Arbor, Mich.; Judith Sebolt-Leopold, Ann Arbor, Mich.; Francis J. Tinney, Ann Arbor, Mich.

[73] Assignee: Warner-Lambert Company, Morris Plains, N.J.

[21] Appl. No.: 667,348

[22] Filed: Jun. 21, 1996

Related U.S. Application Data

[63] Continuation of Ser. No. 353,473, Dec. 9, 1994, abandoned, which is a continuation-in-part of Ser. No. 309,635, Sep. 23, 1994, abandoned, which is a continuation-in-part of Ser. No. 142,756, Oct. 25, 1993, abandoned.

[51] Int. Cl.[6] .................................................. A61K 38/08
[52] U.S. Cl. ............................. 530/330; 514/17; 514/18
[58] Field of Search ............................. 530/330; 514/17, 514/18

[56] References Cited

U.S. PATENT DOCUMENTS

| | | | |
|---|---|---|---|
| 3,880,825 | 4/1975 | Sakakibara | 260/112.5 |
| 4,035,348 | 7/1977 | Tinney et al. | |
| 4,043,993 | 8/1977 | Tinney et al. | |
| 4,062,835 | 12/1977 | Tinney | |
| 4,847,201 | 7/1989 | Kaswasaki | 435/70 |

FOREIGN PATENT DOCUMENTS

| | | |
|---|---|---|
| 0461869 | 12/1991 | European Pat. Off. |
| 0520823 | 12/1992 | European Pat. Off. |
| 0523873 | 1/1993 | European Pat. Off. |
| 0528486 | 2/1993 | European Pat. Off. |
| 0535730 | 4/1993 | European Pat. Off. |
| 0535731 | 4/1993 | European Pat. Off. |
| 9116340 | 10/1991 | WIPO |

OTHER PUBLICATIONS

Vavrek, Life Sciences (Suppl. 1), 451, 1983.
Bodansky, Principles of Peptide Synth (Springer-Verlag) pp. 208–209, 1984.
Bodansky, Principles of Peptide Synth p. 142.
Cell, 65, 1 (1991).
Chimica Oggi, 10, 26 (1992).
Microbiol Rev., 53, 171 (1989).
Hypertension, 13, 706 (1989).
J. Clin. Invest. 83, 1419 (1989).
Hypertension, 14, 358 (1989).
Molec. Cell. Biol., 13, 3706 (1993).
Cell, 57, 1167 (1989).
Science, 245, 379 (1989).
Proc. Natl. Acad. Sci. USA, 86, 8323 (1989).
Bioch. Soc. Trans. 20, 487–88 (1992).
J. Biol. Chem., 268, 9675 (1993).
Science, 260, 1934 (1993).
Science, 260, 1937 (1993).
J. Biol. Chem., 268, 18415 (1993).
PCT International Search Report, PCT/US 94/12060.
Cell, vol. 59, 17 Nov. 1989, pp. 603–614, Kast et al.
Proc. Am. Ass. Cancer Res., vol. 35(0), Mar. 1994, p. 593, Sebolt-Leopold et al.

*Primary Examiner*—Cecilia J. Tsang
*Assistant Examiner*—David Lukton
*Attorney, Agent, or Firm*—Todd M. Crissey

[57] ABSTRACT

Inhibitors of protein:farnesyl transferase enzyme are described, as well as methods for the preparation and pharmaceutical compositions of the same, which are useful in controlling tissue proliferative diseases, including cancer and restenosis.

28 Claims, No Drawings

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
( A ) LENGTH: 4 amino acids
( B ) TYPE: amino acid (D) TOPOLOGY: linear (ii) MOLECULE TYPE: peptide (xi) SEQUENCE DESCRIPTION: SEQ ID NO:1:

Cys Xaa Xaa Xaa
1

(2) INFORMATION FOR SEQ ID NO:2:

(i) SEQUENCE CHARACTERISTICS:
 (A) LENGTH: 4 amino acids
 (B) TYPE: amino acid
 (D) TOPOLOGY: linear (ii) MOLECULE TYPE: peptide (xi) SEQUENCE DESCRIPTION: SEQ ID NO:2:

Cys Xaa Xaa Xaa
1

(2) INFORMATION FOR SEQ ID NO:3:

(i) SEQUENCE CHARACTERISTICS:
 (A) LENGTH: 4 amino acids
 (B) TYPE: amino acid
 (D) TOPOLOGY: linear (ii) MOLECULE TYPE: peptide (xi) SEQUENCE DESCRIPTION: SEQ ID NO:3:

Cys Xaa Xaa Xaa
1

(2) INFORMATION FOR SEQ ID NO:4:

(i) SEQUENCE CHARACTERISTICS:
 (A) LENGTH: 4 amino acids
 (B) TYPE: amino acid
 (D) TOPOLOGY: linear (ii) MOLECULE TYPE: peptide (xi) SEQUENCE DESCRIPTION: SEQ ID NO:4:

Cys Xaa Xaa Xaa
1

(2) INFORMATION FOR SEQ ID NO:5:

(i) SEQUENCE CHARACTERISTICS:
 (A) LENGTH: 5 amino acids
 (B) TYPE: amino acid
 (D) TOPOLOGY: linear (ii) MOLECULE TYPE: peptide (xi) SEQUENCE DESCRIPTION: SEQ ID NO:5:

His Xaa Xaa Trp Ala
1               5

(2) INFORMATION FOR SEQ ID NO:6:

(i) SEQUENCE CHARACTERISTICS:
 (A) LENGTH: 5 amino acids
 (B) TYPE: amino acid
 (D) TOPOLOGY: linear (ii) MOLECULE TYPE: peptide (xi) SEQUENCE DESCRIPTION: SEQ ID NO:6:

His Xaa Xaa Trp Ala
1               5

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

His Xaa Xaa Trp Ala
1               5

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

His Xaa Xaa Trp Ala
1               5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

His Xaa Xaa Trp Ala
1               5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

His Xaa Xaa Trp Ala
1               5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

His Xaa Xaa Trp Gly
1               5

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

His  Xaa  Xaa  Trp  Gly
    1                         5

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

His  Xaa  Xaa  Trp  Gly
    1                         5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

His  Xaa  Xaa  Trp  Gly
    1                         5

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

His  Xaa  Xaa  Trp  Gly
    1                         5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

His  Xaa  Xaa  Trp  Gly
    1                         5

( 2 ) INFORMATION FOR SEQ ID NO:17:

( i ) SEQUENCE CHARACTERISTICS:
        ( A ) LENGTH: 5 amino acids
        ( B ) TYPE: amino acid (D) TOPOLOGY: linear (i i) MOLECULE TYPE: peptide (x i) SEQUENCE DESCRIPTION: SEQ ID NO:17:

His Phe Xaa Trp Ala
1             5

(2) INFORMATION FOR SEQ ID NO:18:

(i) SEQUENCE CHARACTERISTICS:
      (A) LENGTH: 4 amino acids
      (B) TYPE: amino acid
      (D) TOPOLOGY: linear (i i) MOLECULE TYPE: peptide (x i) SEQUENCE DESCRIPTION: SEQ ID NO:18:

His Xaa Xaa Trp
1

(2) INFORMATION FOR SEQ ID NO:19:

(i) SEQUENCE CHARACTERISTICS:
      (A) LENGTH: 4 amino acids
      (B) TYPE: amino acid
      (D) TOPOLOGY: linear (i i) MOLECULE TYPE: peptide (x i) SEQUENCE DESCRIPTION: SEQ ID NO:19:

His Xaa Xaa Trp
1

(2) INFORMATION FOR SEQ ID NO:20:

(i) SEQUENCE CHARACTERISTICS:
      (A) LENGTH: 4 amino acids
      (B) TYPE: amino acid
      (D) TOPOLOGY: linear (i i) MOLECULE TYPE: peptide (x i) SEQUENCE DESCRIPTION: SEQ ID NO:20:

His Xaa Cys Trp
1

(2) INFORMATION FOR SEQ ID NO:21:

(i) SEQUENCE CHARACTERISTICS:
      (A) LENGTH: 4 amino acids
      (B) TYPE: amino acid
      (D) TOPOLOGY: linear (i i) MOLECULE TYPE: peptide (x i) SEQUENCE DESCRIPTION: SEQ ID NO:21:

His Xaa Cys Trp
1

(2) INFORMATION FOR SEQ ID NO:22:

(i) SEQUENCE CHARACTERISTICS:
      (A) LENGTH: 5 amino acids
      (B) TYPE: amino acid
      (D) TOPOLOGY: linear (i i) MOLECULE TYPE: peptide (x i) SEQUENCE DESCRIPTION: SEQ ID NO:22:

His Xaa Xaa Trp Ala
1               5

(2) INFORMATION FOR SEQ ID NO:23:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:23:

His Xaa Xaa Trp Ala
1               5

(2) INFORMATION FOR SEQ ID NO:24:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:24:

His Xaa Xaa Trp Ala
1               5

(2) INFORMATION FOR SEQ ID NO:25:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:25:

His Xaa Xaa Trp Ala
1               5

(2) INFORMATION FOR SEQ ID NO:26:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:26:

His Xaa Xaa Trp Ala
1               5

(2) INFORMATION FOR SEQ ID NO:27:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:27:

His Xaa Xaa Trp Ala
1               5

( 2 ) INFORMATION FOR SEQ ID NO:28:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

His  Xaa  Xaa  Trp  Gly
    1                          5

( 2 ) INFORMATION FOR SEQ ID NO:29:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

His  Xaa  Xaa  Trp  Gly
    1                          5

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

His  Xaa  Xaa  Trp  Gly
    1                          5

( 2 ) INFORMATION FOR SEQ ID NO:31:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

His  Xaa  Xaa  Trp  Gly
    1                          5

( 2 ) INFORMATION FOR SEQ ID NO:32:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

His  Xaa  Xaa  Trp  Gly
    1                          5

( 2 ) INFORMATION FOR SEQ ID NO:33:

( i ) SEQUENCE CHARACTERISTICS:
        ( A ) LENGTH: 5 amino acids
        ( B ) TYPE: amino acid (D) TOPOLOGY: linear (ii) MOLECULE TYPE: peptide (xi) SEQUENCE DESCRIPTION: SEQ ID NO:33:

His Xaa Xaa Trp Gly
1               5

(2) INFORMATION FOR SEQ ID NO:34:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:34:

His Xaa Cys Trp Ala
1               5

(2) INFORMATION FOR SEQ ID NO:35:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:35:

His Xaa Cys Trp Ala
1               5

(2) INFORMATION FOR SEQ ID NO:36:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:36:

His Xaa Cys Trp Ala
1               5

(2) INFORMATION FOR SEQ ID NO:37:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:37:

His Xaa Cys Trp Ala
1               5

(2) INFORMATION FOR SEQ ID NO:38:

(i) SEQUENCE CHARACTERISTICS:
      (A) LENGTH: 5 amino acids
      (B) TYPE: amino acid
      (D) TOPOLOGY: linear (ii) MOLECULE TYPE: peptide (xi) SEQUENCE DESCRIPTION: SEQ ID NO:38:

His Xaa Cys Trp Ala
1               5

( 2 ) INFORMATION FOR SEQ ID NO:39:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:39:

His Xaa Cys Trp Ala
1               5

( 2 ) INFORMATION FOR SEQ ID NO:40:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:40:

His Xaa Cys Trp Gly
1               5

( 2 ) INFORMATION FOR SEQ ID NO:41:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:41:

His Xaa Cys Trp Gly
1               5

( 2 ) INFORMATION FOR SEQ ID NO:42:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

His Xaa Cys Trp Gly
1               5

( 2 ) INFORMATION FOR SEQ ID NO:43:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:43:

His Xaa Cys Trp Gly
1               5

( 2 ) INFORMATION FOR SEQ ID NO:44:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:44:

His Xaa Cys Trp Gly
    1                   5

( 2 ) INFORMATION FOR SEQ ID NO:45:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:45:

His Xaa Cys Trp Gly
    1                   5

( 2 ) INFORMATION FOR SEQ ID NO:46:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:

His Xaa Cys Trp Ala
    1                   5

( 2 ) INFORMATION FOR SEQ ID NO:47:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:47:

His Xaa Cys Trp Ala
    1                   5

( 2 ) INFORMATION FOR SEQ ID NO:48:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:48:

His Xaa Cys Trp Ala
    1                   5

( 2 ) INFORMATION FOR SEQ ID NO:49:

( i ) SEQUENCE CHARACTERISTICS:
        ( A ) LENGTH: 5 amino acids
        ( B ) TYPE: amino acid (D) TOPOLOGY: linear (ii) MOLECULE TYPE: peptide (xi) SEQUENCE DESCRIPTION: SEQ ID NO:49:

His Xaa Cys Trp Ala
1               5

(2) INFORMATION FOR SEQ ID NO:50:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:50:

His Xaa Cys Trp Ala
1               5

(2) INFORMATION FOR SEQ ID NO:51:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:51:

His Xaa Cys Trp Ala
1               5

(2) INFORMATION FOR SEQ ID NO:52:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:52:

His Xaa Cys Trp Gly
1               5

(2) INFORMATION FOR SEQ ID NO:53:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:53:

His Xaa Cys Trp Gly
1               5

(2) INFORMATION FOR SEQ ID NO:54:

(i) SEQUENCE CHARACTERISTICS:
    (A) LENGTH: 5 amino acids
    (B) TYPE: amino acid
    (D) TOPOLOGY: linear (ii) MOLECULE TYPE: peptide (xi) SEQUENCE DESCRIPTION: SEQ ID NO:54:

His Xaa Cys Trp Gly
1               5

(2) INFORMATION FOR SEQ ID NO:55:

(i) SEQUENCE CHARACTERISTICS:
  (A) LENGTH: 5 amino acids
  (B) TYPE: amino acid
  (D) TOPOLOGY: linear (ii) MOLECULE TYPE: peptide (xi) SEQUENCE DESCRIPTION: SEQ ID NO:55:

His Xaa Cys Trp Gly
1               5

(2) INFORMATION FOR SEQ ID NO:56:

(i) SEQUENCE CHARACTERISTICS:
  (A) LENGTH: 5 amino acids
  (B) TYPE: amino acid
  (D) TOPOLOGY: linear (ii) MOLECULE TYPE: peptide (xi) SEQUENCE DESCRIPTION: SEQ ID NO:56:

His Xaa Cys Trp Gly
1               5

(2) INFORMATION FOR SEQ ID NO:57:

(i) SEQUENCE CHARACTERISTICS:
  (A) LENGTH: 5 amino acids
  (B) TYPE: amino acid
  (D) TOPOLOGY: linear (ii) MOLECULE TYPE: peptide (xi) SEQUENCE DESCRIPTION: SEQ ID NO:57:

His Xaa Cys Trp Gly
1               5

(2) INFORMATION FOR SEQ ID NO:58:

(i) SEQUENCE CHARACTERISTICS:
  (A) LENGTH: 4 amino acids
  (B) TYPE: amino acid
  (D) TOPOLOGY: linear (ii) MOLECULE TYPE: peptide (xi) SEQUENCE DESCRIPTION: SEQ ID NO:58:

His Xaa Xaa Trp
1

(2) INFORMATION FOR SEQ ID NO:59:

(i) SEQUENCE CHARACTERISTICS:
  (A) LENGTH: 6 amino acids
  (B) TYPE: amino acid
  (D) TOPOLOGY: linear (ii) MOLECULE TYPE: peptide (xi) SEQUENCE DESCRIPTION: SEQ ID NO:59:

Tyr Lys Cys Val Ile Met
1               5

SUBSTITUTED TETRA- AND PENTAPEPTIDE INHIBITORS OF PROTEIN: FARNESYL TRANSFERASE

CROSS-REFERENCE TO RELATED APPLICATIONS

This application is a continuation of U.S. application Ser. No. 08/353,473, filed Dec. 9, 1994, now abandoned, which is a continuation-in-part of U.S. application Ser. No. 08/309, 635 filed Sep. 23, 1994, now abandoned, which is a continuation-in-part of U.S. application Ser. No. 08/142,756 filed Oct. 25, 1993, now abandoned.

FIELD OF THE INVENTION

The present invention pertains to a number of compounds which can be used in the medicinal field to treat, prophylactically or otherwise, uncontrolled or abnormal proliferation of human tissues. More specifically, the present invention pertains to a number of compounds which act to inhibit the farnesyl transferase enzyme that has been determined to activate ras proteins which in turn activate cellular division and are implicated in cancer and restenosis.

BACKGROUND OF THE INVENTION

Ras protein (or p21) has been examined extensively because mutant forms are found in 20% of most types of human cancer and greater than 50% of colon and pancreatic carcinomas (J. B. Gibbs, *Cell* 65, 1 (1991), T. Cartwright, et al., *Chimica Oggi* 10, 26 (1992)). These mutant ras proteins are deficient in the capability for feedback regulation that is present in native ras and this deficiency is associated with their oncogenic action since the ability to stimulate normal cell division can not be controlled by the normal endogenous regulatory cofactors. The recent discovery that the transforming activity of mutant ras is critically dependent on posttranslational modifications (J. Gibbs, et al., *Microbiol. Rev.* 53, 171 (1989)) has unveiled an important aspect of ras function and identified novel prospects for cancer therapy.

In addition to cancer, there are other conditions of uncontrolled cellular proliferation that are related to excessive expression and/or function of native ras proteins. Post surgical vascular restenosis is such a condition. The use of various surgical revascularization techniques such as saphenous vein bypass grafting, endarterectomy and transluminal coronary angioplasty is often accompanied by complications due to uncontrolled growth of neointimal tissue, known as restenosis. The biochemical causes of restenosis are poorly understood and numerous growth factors and protooncogenes have been implicated (A. J. Naftilan, et al., *Hypertension* 13, 706 (1989) and *J. Clin. Invest.* 83, 1419; G. H. Gibbons, et al., *Hypertension* 14, 358 (1989); T. Satoh, et al., *Mollec. Cell. Biol.* 13, 3706 (1993)). The fact that ras proteins are known to be involved in cell division processes makes them a candidate for intervention in many situations where cells are dividing uncontrollably. In direct analogy to the inhibition of mutant ras related cancer, blockade of ras dependant processes has the potential to reduce or eliminate the inappropriate tissue proliferation associated with restenosis, particularly in those instances where normal ras expression and/or function is exaggerated by growth stimulatory factors.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of posttranslational processing steps that are signaled by a carboxyl terminal amino acid consensus sequence that is recognized by protein:farnesyl transferase. This consensus sequence consists of a cysteine residue located four amino acids from the carboxyl terminus, followed by two lipophilic amino acids and the C-terminal residue. The sulfhydryl group of the cysteine residue is alkylated by farnesyl pyrophosphate in a reaction that is catalyzed by protein:farnesyl transferase. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these posttranslational modifications are essential for transforming activity. Replacement of the consensus sequence cysteine residue with other amino acids gives a ras protein that is no longer farnesylated, fails to migrate to the cell membrane and lacks the ability to stimulate cell proliferation (J. F. Hancock, et al., *Cell* 57, 1617 (1989), W. R. Schafer, et al., *Science* 245, 379 (1989), P. J. Casey, *Proc. Natl. Acad. Sci. USA* 86, 8323 (1989)).

Recently, protein:farnesyl transferases (PFTs, also referred to as farnesyl:protein transferases) have been identified and a specific PFT from rat brain was purified to homogeneity (Y. Reiss, et al., *Bioch. Soc. Trans.* 20, 487–88 (1992)). The enzyme was characterized as a heterodimer composed of one alpha-subunit (49 kDa) and one beta-subunit (46 kDa), both of which are required for catalytic activity. High level expression of mammalian PFT in a baculovirus system and purification of the recombinant enzyme in active form has also been accomplished (W.-J. Chen, et al., *J. Biol. Chem.* 268, 9675 (1993)).

In light of the foregoing, the discovery that the function of oncogenic ras proteins is critically dependent on their posttranslational processing provides a means of cancer chemotherapy through inhibition of the processing enzymes. The identification and isolation of a protein:farnesyl transferase that catalyzes the addition of a farnesyl group to ras proteins provides a promising target for such intervention. Recently it has been determined that prototypical inhibitors of PFT can inhibit ras processing and reverse cancerous morphology in tumor cell models (N. E. Kohl, et al., *Science* 260, 1934 (1993), G. L. James, et al., *Science* 260, 1937 (1993), A. M. Garcia, et al., *J. Biol. Chem.* 268, 18415 (1993)). Thus, it is possible to prevent or delay the onset of cellular proliferation in cancers that exhibit mutant ras proteins by blocking PFT. By analogous logic, inhibition of PFT would provide a potential means for controlling cellular proliferation associated with restenosis, especially in those cases wherein the expression and/or function of native ras is overstimulated.

PCT Application WO91/16340 discloses cysteine containing tetrapeptide inhibitors of PFT of the formula CAAX Seq ID NO:1.

European Patent Application 0461869 discloses cysteine containing tetrapeptide inhibitors of PFT of the formula Cys-Aaa$^1$-Aaa$^2$-Xaa Seq ID NO:2.

European Patent Application 0520823 discloses cysteine containing tetrapeptide inhibitors of PFT of the formula Cys-Xaa$^1$-dXaa$^2$-Xaa$^3$.

European Patent Application 0523873 discloses cysteine containing tetrapeptide inhibitors of PFT of the formula Cys-Xaa$^1$-Xaa$^2$-Xaa$^3$ Seq ID NO:3.

European Patent Application 0528486 discloses cysteine containing tetrapeptide amides inhibitors of PFT of the formula Cys-Xaa¹-Xaa²-Xaa³-NRR¹ Seq ID NO:3.

European Patent Application 0535730 discloses pseudotetrapeptide inhibitors of PFT of the following two formulas:

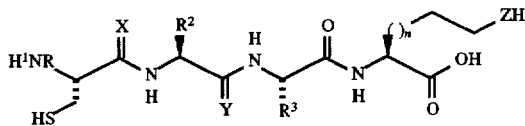

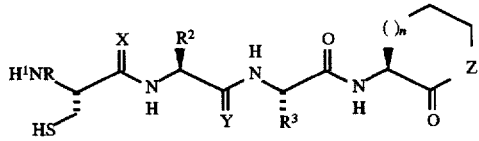

European Patent Application 0535731 (U.S. Pat. No. 5,238,922) discloses esters of pseudotetrapeptide inhibitors of PFT of the formula:

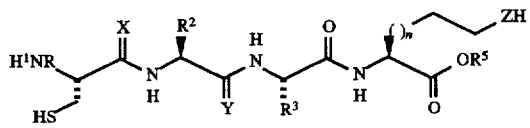

U.S. Pat. No. 4,035,348 discloses tetrapeptide antagonists of luteinizing hormone releasing factor of the formula A-R$_1$-Tyr(benzyl)-Ser(benzyl)-D-Ala-R$_2$, wherein one of the definitions of R$_1$ is L-His(benzyl).

U.S. Pat. No. 4,043,993 discloses pentapeptide antagonists of luteinizing hormone releasing factor of the formula X-R-Tyr(benzyl)-Ser(benzyl)-R¹-Y, wherein one of the definitions of R is His(benzyl).

U.S. Pat. No. 4,062,835 discloses pentapeptide antagonists of luteinizing hormone releasing factor of the formula X-R-Tyr(methyl)-Ser(benzyl)-R¹-Y, wherein one of the definitions of R is His(benzyl).

Compounds disclosed in the above references do not disclose or suggest a novel combination of structural variations found in the present invention described hereinafter.

SUMMARY OF THE INVENTION

Accordingly, the present invention is a substituted tetra- or pentapeptide compound of Formula I:

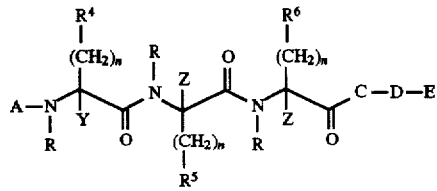

wherein
n=1 or 2;
A=—COR², —CO$_2$R², —CONHR², —CSR², —C(S)R², —C(S)NHR², or H;
wherein R² is alkyl, —(CH$_2$)$_m$-cycloalkyl, —(CH$_2$)$_m$-aryl, —(CH$_2$)$_m$-heteroaryl, and m=0, 1, 2, or 3;
R=independently H or Me;
Y=independently H or Me;
Z=independently H or Me;

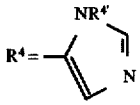

wherein R⁴'=H or Me;
—SR⁴", wherein R⁴"=H, alkyl, trityl, or heteroaryl;

wherein R⁵'=H, —OH, —O-alkyl, alkyl, —CO-aryl, —(CH$_2$)$_m$-aryl, —O(CH$_2$)$_m$-cycloalkyl, —O(CH$_2$)$_m$-aryl, —O(CH$_2$)$_m$-heteroaryl, —OPO$_3$R⁵"$_2$, —CH$_2$PO$_3$R⁵"$_2$, —CF$_2$PO$_3$R⁵"$_2$, or —CFHPO$_3$R⁵"$_2$, wherein R⁵' is located at either the ortho, meta, or para position and R⁵"=H, alkyl, alkylaryl, or cyclohexyl, and m is as described above;
—COOR⁷, wherein R⁷=H, Me, t-butyl, or benzyl;
—SR⁸, wherein R⁸=H or trityl;
R⁶=OR⁶', wherein R⁶'=H, benzyl, —PO$_3$R⁵"$_2$, wherein R⁵" is as described above;
—CH$_2$—R⁹, wherein R⁹=—PO$_3$R⁵"$_2$, wherein R⁵" is as described above;
—SR⁶", wherein R⁶"=H, benzyl, or trityl;
C=Gly, Ala, Val, Leu, Ile, Phe, Tyr, Tyr(OMe), Pgl, homoPhe, Trp, Trp(Me), or Trp(CHO);
D=Gly, Ala, or absent;
E=—OH, —NH$_2$, —NHNH$_2$, —NHR¹⁰, or —OR¹⁰,
wherein R¹⁰=H, alkyl, —(CH$_2$)$_m$-cycloalkyl, —(CH$_2$)$_m$-aryl, —(CH$_2$)$_m$- heteroaryl, and m is as described above; an isomer or a pharmaceutically acceptable salt thereof.

The present invention is also directed to the use of a compound of Formula I, or a pharmaceutically acceptable salt therefrom, to inhibit the activity of a protein:farnesyl transferase enzyme as a method for treating tissue proliferative diseases.

A further embodiment of the present invention is the use of a pharmaceutical composition including an effective amount of a compound of Formula I as a method for the treatment of cancer.

A still further embodiment of the present invention is the use of a pharmaceutical composition including an effective amount of a compound of Formula I as a method for the treatment of restenosis.

A still further embodiment of the present invention is a pharmaceutical composition for administering an effective amount of a compound of Formula I in unit dosage form in the treatment methods mentioned above.

A final embodiment of the present invention pertains to methods for the preparation of compounds of Formula I by solid phase synthesis and solution phase synthesis.

DETAILED DESCRIPTION OF THE PREFERRED EMBODIMENTS

In the compounds of Formula I, the term "alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "cycloalkyl" means a saturated hydrocarbon ring which contains from 3 to 10 carbon atoms, for example, cyclopropyl, cyclobutyl, cyclopentyl, cyclohexyl, adamantyl, and the like.

The term "aryl" means an aromatic ring which is a phenyl, 5-fluorenyl, 1-naphthyl or 2-naphthyl group, unsubstituted or substituted by 1 to 3 substituents selected from alkyl, O-alkyl and S-alkyl, —OH, —SH, —F, —Cl, —Br, —I, —CF$_3$, —NO$_2$, —NH$_2$, —NHCH$_3$, —N(CH$_3$)$_2$, —NHCO-alkyl, —(CH$_2$)$_m$CO$_2$H, —(CH$_2$)$_m$CO$_2$-alkyl, —(CH$_2$)$_m$SO$_3$H, —(CH$_2$)$_m$PO$_3$H$_2$, —(CH$_2$)$_m$PO$_3$(alkyl)$_2$, —(CH$_2$)$_m$SO$_2$NH$_2$, and —(CH$_2$)$_m$SO$_2$NH-alkyl wherein alkyl is defined as above and m=0, 1, 2, or 3.

The term "alkylaryl" means alkyl as defined above and aryl as defined above, for example, benzyl.

The term "heteroaryl" means a heteroaromatic ring which is a 2- or 3-thienyl, 2- or 3-furanyl, 2- or 3-pyrrolyl, 2-, 3- or 4-pyridyl, 2-, 3-, 4-, 5-, 6- or 7-indolyl group, substituted or unsubstituted by 1 or 2 substituents from the group of substituents described above for aryl.

The following table provides a list of abbreviations and definitions thereof used in the present invention.

TABLE OF ABBREVIATIONS

| Abbreviation* | Amino Acid |
|---|---|
| Ala | Alanine |
| Arg | Arginine |
| Asn | Asparagine |
| Asp | Aspartic acid |
| Cys | Cysteine |
| Glu | Glutamic acid |
| Gln | Glutamine |
| Gly | Glycine |
| His | Histidine |
| Ile | Isoleucine |
| Leu | Leucine |
| Lys | Lysine |
| Met | Methionine |
| Phe | Phenylalanine |
| Pro | Proline |
| Ser | Serine |
| Thr | Threonine |
| Trp | Tryptophan |
| Tyr | Tyrosine |
| Val | Valine |

| Abbreviation* | Modified and Unusual Amino Acid |
|---|---|
| Aaa-OR | An amino acid ester, for examples: Gly-OMe is Glycine, methyl ester; D-Ala-COMe is D-Alanine, methyl ester. |
| Aaa-NHR | An amino acid amide, for examples: D-Ala-NHEt is D-Alanine, N-ethyl amide; Trp-NH$_2$ is Tryptophanamide. |
| 3Hyp | 3-Hydroxyproline |
| 4Hyp | 4-Hydroxyproline |
| Hcy | Homocysteine |
| Nva | Norvaline |
| Nle | Norleucine |
| Orn | Ornithine |
| Bal | Beta-alanine (or 3-aminopropionic acid) |
| Abu | 4-Aminobutyric acid |
| Ahe | 7-Aminoheptanoic acid |
| Acp | 6-Aminocaproic acid |
| Aoc | 8-Aminooctanoic acid |
| Apn | 5-Aminopentanoic acid |
| Bpa | (4-Benzoylphenyl) alanine |
| Chx | 3-Cyclohexylalanine (or Hexahydrophenylalanine) |
| Cit | Citrulline |
| His(1-Me) | 1-Methyl-histidine (or N(τ)-Methyl-histidine) |
| His(Tr) | 1-Triphenylmethyl-histidine (or N(τ)-Trityl-histidine) |
| homoPhe | 2-Amino-4-phenylbutanoic acid (or Homophenylalanine) |
| homoTyr | 2-Amino-4-(4-hydroxyphenyl)butanoic acid (or Homotyrosine) |
| homoTyr(OBn) | 2-Amino-4-[4-(phenylmethoxy)phenyl]-butanoic acid (or O-Benzyl-homotyrosine) |
| 1-Nal | 3-(1'-Naphthyl)alanine |
| 2-Nal | 3-(2'-Naphthyl)alanine |
| Pen | Penicillamine |
| Phe(3-OBn) | (3-Benzyloxyphenyl)alanine |
| Phe(4-Ph) | 3-(1,1'Biphen-4-yl)alanine (or 4-Phenyl-phenylalanine) |
| Pgl | Phenylglycine |
| Pyr | 2-Amino-3-(3-pyridyl)-propanoic acid (or 3-Pyridylalanine) |
| Ser(OBn) | O-Benzyl-serine |
| Thr(OBn) | O-Benzyl-threonine |
| Tic | 1,2,3,4-Tetrahydro-3-isoquinoline-carboxylic acid |
| Tyr(OMe) | O-Methyl-tyrosine |
| Tyr(OEt) | O-Ethyl-tyrosine |
| Tyr(OBn) | O-Benzyl-tyrosine |
| (α-Me)Tyr(OBn) | 2-Amino-3-(4-benzyloxyphenyl)-2-methyl-propionic acid (or α-Methyl-O-benzyl-tyrosine) |
| (N-Me)Tyr(OBn) | N-Methyl-O-benzyl-tyrosine |
| Trp(For) | N$^{in}$-Formyltryptophan |

| Abbreviation | Mercapto Acids |
|---|---|
| Maa | Mercaptoacetic acid |
| Mba | 4-Mercaptobutyric acid |
| Mpa | 3-Mercaptopropionic acid |

| Abbreviation | Protecting Group |
|---|---|
| Ac | Acetyl |
| Ada | 1-Adamantyl acetic acid |
| Adoc | Adamantyloxycarbonyl |
| Bn | Benzyl |
| MeBn | 4-Methylbenzyl |
| Cbz | Benzyloxycarbonyl |
| 2-Br-Cbz | ortho-Bromobenzyloxycarbonyl |
| 2-Cl-Cbz | ortho-Chlorobenzyloxycarbonyl |
| Bom | Benzyloxymethyl |
| Boc | tertiary Butyloxycarbonyl |
| Dnp | 2,4-Dinitrophenyl |
| For | Formyl |
| Fmoc | 9-Fluorenylmethyloxycarbonyl |
| NO$_2$ | Nitro |
| Tos | 4-Toluenesulfonyl (tosyl) |
| Tr | Triphenylmethyl (trityl) |

| Abbreviation | Solvents and Reagents |
|---|---|
| HOAC | Acetic acid |
| CF$_3$SO$_2$H | Trifluoromethanesulfonic acid |
| DCM | Dichloromethane |
| DCC | N,N'-Dicyclohexylcarbodiimide |
| DIC | N,N'-Diisopropylcarbodiimide |
| DIEA | N,N-Diisopropylethylamine |
| DMAP | 4-Dimethylaminopyridine |
| DMF | N,N'-Dimethylformamide |
| EDAC | N-Ethyl-N'-Dimethylaminopropylcarbodiimide |
| EtOAc | Ethyl acetate |
| Et$_2$O | Diethyl ether |
| HCl | Hydrochloric acid |
| HF | Hydrofluoric acid |
| HOBT | 1-Hydroxybenzotriazole |
| KOH | Potassium hydroxide |
| MeCN | Acetonitrile |
| MeOH | Methanol |
| NHOS | N-Hydroxysuccinimide |
| NMP | N-Methylpyrrolidone |
| iPrOH | iso-Propanol |
| TFA | Trifluoroacetic acid |

TABLE OF ABBREVIATIONS-continued

| Abbreviation | Solid Phase Peptide Synthesis Resins |
|---|---|
| HMP Resin | 4-(Hydroxymethyl)-phenoxymethyl-poly styrene resin |
| MBHA Resin | Methylbenzhydrylamine resin |
| PAM Resin | 4-(Hydroxymethyl)-phenylacetamidomethyl-polystyrene resin |
| 2-Cl-Tr Resin | 2-Chlorotrityl-polystyrene resin |
| NH$_2$-Rink Resin | 4-(amino-(2',4'-dimethoxyphenyl)-methyl)-phenoxymethyl-polystyrene resin |

| Abbreviation | Biological Reagents |
|---|---|
| FPP | Farnesyl pyrophosphate |
| PFT | Protein:farnesyl transferase |
| DTT | Dithiothreitol |
| BSA | Bovine serum albumin |

| Abbreviation | Miscellaneous |
|---|---|
| COR$^2$ | $-\overset{O}{\underset{\|}{C}}R^2$ |
| CO$_2$R$^2$ | $-\overset{O}{\underset{\|}{C}}OR^2$ |
| CONHR$^2$ | $-\overset{O}{\underset{\|}{C}}NHR^2$ |
| CSR$^2$ | $-\overset{S}{\underset{\|}{C}}R^2$ |
| C(S)OR$^2$ | $-\overset{S}{\underset{\|}{C}}OR^2$ |
| C(S)NHR$^2$ | $-\overset{S}{\underset{\|}{C}}NHR^2$ |
| CONH$_2$ | $-\overset{O}{\underset{\|}{C}}NH_2$ |
| CONHNH$_2$ | $-\overset{O}{\underset{\|}{C}}NHNH_2$ |
| CONHR$^2$ | $-\overset{O}{\underset{\|}{C}}NHR^2$ |

*If the optical activity of the amino acid is other than L(S), the amino acid or abbreviation is preceded by the appropriate configuration D(R) or DL(RS).

Preferred compounds of the invention are designated by Formula II:

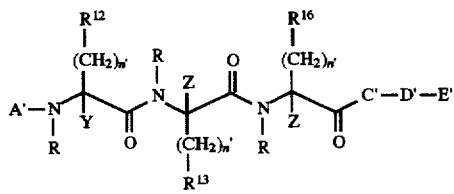

wherein
n'=1 or 2;
A'=—COR$^{2'}$, —CO$_2$R$^{2'}$, or —CONHR$^{2'}$, wherein R$^{2'}$=alkyl, —(CH$_2$)$_m$-aryl, —(CH$_2$)$_m$-heteroaryl, and m=0, 1, or 2;
R=independently H or Me;
Y=independently H or Me;
Z=independently H or Me;

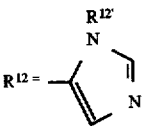

wherein R$^{12'}$=H or Me; —SR$^{12''}$, wherein R$^{12''}$=H or alkyl;

wherein R$^{13'}$=H, —OH, —O-alkyl, alkyl, —CO-aryl, benzyl, —O-benzyl, wherein R$^{13'}$ is located at either the ortho, meta, or para position;
—OPO$_3$R$^{14}$$_2$, —CH$_2$PO$_3$R$^{14}$$_2$, or —CF$_2$PO$_3$R$^{14}$$_2$, wherein R$^{14}$=H or alkyl;
—COOR$^{15}$, wherein R$^{15}$=H, Me, t-butyl, or benzyl;
R$^{16}$=—OR$^{16'}$, wherein R$^{16'}$=H, benzyl, —PO$_3$R$^{14}$$_2$, wherein R$^{14}$ is as described above;
—CH$_2$—R$^{16''}$, wherein R$^{16''}$=—PO$_3$R$^{14}$$_2$, wherein R$^{14}$ is as described above;
—SR$^{16'''}$, wherein R$^{16'''}$=H or benzyl;
C'=Ala, Trp, Trp(Me), or Trp(CHO);
D'=Gly, Ala, or absent;
E'=—OMe, —NH$_2$, —NHNH$_2$, —OH or NH-alkyl; an isomer or a pharmaceutically acceptable salt thereof.

Other preferred compounds of the present invention are those of Formula I as defined above wherein A is Cbz, BnNHCO, R is H and n is 1 or 2; or as defined above wherein R$^4$ is

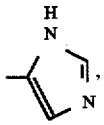

—SH and Y is H;
or as defined above wherein wherein R$^5$ is

wherein R$^{5'}$ is H, —OH, —OBn, —OPO$_3$H$_2$, —CH$_2$PO$_3$H$_2$, —CH$_2$PO$_3$Et$_2$, —CF$_2$PO$_3$H$_2$, or wherein R$^{5}$=—COOH, and Z is H;
or as defined above wherein R$^6$ is —OBn, —OH, —SH, or —OPO$_3$H$_2$; or as defined above wherein C is Trp or Ala; or as defined above wherein D is Ala, Gly, or absent;
or as defined above wherein E is —OH, —NH$_2$, —OMe, —NHEt, —NHNH$_2$, or —NHMe.

Most preferred compounds of the invention include the following Seq ID NO:5
Cbz-His-Tyr(OBn)-Ser(OBn)-Trp-D-Ala-NH$_2$;
Cbz-His-Tyr(OBn)-Ser(OBn)-Trp-D-Ala-NHMe;
Cbz-His-Tyr(OBn)-Ser(OBn)-Trp-D-Ala-NHEt;
Cbz-His-Tyr(OBn)-Ser(OBn)-Trp-D-Ala-NHNH$_2$;
Cbz-His-Tyr(OBn)-Ser(OBn)-Trp-D-Ala-OMe;
Cbz-His-Tyr(OBn)-Ser(OBn)-Trp-D-Ala;
Cbz-His-Tyr(OBn)-Ser(OBn)-Trp-Ala-NH$_2$;

Cbz-His-Tyr(OBn)-Ser(OBn)-Trp-Ala-NHMe Seq ID NO:6;
Cbz-His-Tyr(OBn)-Ser(OBn)-Trp-Ala-NHEt Seq ID NO:7;
Cbz-His-Tyr(OBn)-Ser(OBn)-Trp-Ala-NHNH$_2$ Seq ID NO:8;
Cbz-His-Tyr(OBn)-Ser(OBn)-Trp-Ala-OMe Seq ID NO:9;
Cbz-His-Tyr(OBn)-Ser(OBn)-Trp-Ala Seq ID NO:10;
Cbz-His-Tyr(OBn)-Ser(OBn)-Trp-Gly-NH$_2$ Seq ID NO:11;
Cbz-His-Tyr(OBn)-Ser(OBn)-Trp-Gly-NHMe Seq ID NO:12;
Cbz-His-Tyr(OBn)-Ser(OBn)-Trp-Gly-NHEt Seq ID NO:13;
Cbz-His-Tyr(OBn)-Ser(OBn)-Trp-Gly-NHNH$_2$ Seq ID NO:14;
Cbz-His-Tyr(OBn)-Ser(OBn)-Trp-Gly-OMe Seq ID NO:15;
Cbz-His-Tyr(OBn)-Ser(OBn)-Trp-Gly Seq ID NO:16;
Cbz-His-Tyr-Ser(OBn)-Trp-D-Ala-NH$_2$;
Cbz-His-Tyr(OBn)-Ser-Trp-D-Ala-NH$_2$;
Cbz-His-Phe-Ser(OBn)-Trp-D-Ala-NH$_2$;
Cbz-His-Phe-Ser(OBn)-Trp-Ala-NH$_2$ Seq ID NO:17;
Cbz-His-Tyr(OBn)-Ser(OBn)-Ala-D-Ala-NH$_2$;
Cbz-D-His-Tyr(OBn)-Ser(OBn)-Trp-D-Ala-NH$_2$;
Cbz-His-D-Tyr(OBn)-Ser(OBn)-Trp-D-Ala-NH$_2$;
Cbz-His-Tyr(OBn)-Ser(OBn)-Trp-OMe Seq ID NO:18;
Cbz-His-Tyr(OBn)-Ser(OBn)-Trp-NH$_2$ Seq ID NO:19;
Cbz-His-Tyr(OBn)-Ser(OBn)-D-Ala-OMe;
Cbz-His-Tyr(OBn)-Ser(OBn)-D-Ala;
Cbz-D-His-Tyr(OBn)-Ser(OBn)-Trp-OMe;
Cbz-His-D-Tyr(OBn)-Ser(OBn)-Trp-OMe;
Cbz-His-Tyr(OBn)-Cys-Trp-NH$_2$ Seq ID NO:20;
BnNHCO-His-Tyr(OBn)-Cys-Trp-NH$_2$ Seq ID NO:21;
BnNHCO-His-Tyr(OBn)-Ser(OBn)-Trp-D-Ala-NH$_2$;
BnNHCO-His-Tyr(OBn)-Ser(OBn)-Trp-D-Ala-NHMe;
BnNHCO-His-Tyr(OBn)-Ser(OBn)-Trp-D-Ala-NHEt;
BnNHCO-His-Tyr(OBn)-Ser(OBn)-Trp-D-Ala-NHNH$_2$;
BnNHCO-His-Tyr(OBn)-Ser(OBn)-Trp-D-Ala-OMe;
BnNHCO-His-Tyr(OBn)-Ser(OBn)-Trp-D-Ala;
BnNHCO-His-Tyr(OBn)-Ser(OBn)-Trp-Ala-NH$_2$ Seq ID NO:22;
BnNHCO-His-Tyr(OBn)-Ser(OBn)-Trp-Ala-NHMe Seq ID NO:23;
BnNHCO-His-Tyr(OBn)-Ser(OBn)-Trp-Ala-NHEt Seq ID NO:24;
BnNHCO-His-Tyr(OBn)-Ser(OBn)-Trp-Ala-NHNH$_2$ Seq ID NO:25;
BnNHCO-His-Tyr(OBn)-Ser(OBn)-Trp-Ala-OMe Seq ID NO:26;
BnNHCO-His-Tyr(OBn)-Ser(OBn)-Trp-Ala Seq ID NO:27;
BnNHCO-His-Tyr(OBn)-Ser(OBn)-Trp-Gly-NH$_2$ Seq ID NO:28;
BnNHCO-His-Tyr(OBn)-Ser(OBn)-Trp-Gly-NHMe Seq ID NO:29;
BnNHCO-His-Tyr(OBn)-Ser(OBn)-Trp-Gly-NHEt Seq ID NO:30;
BnNHCO-His-Tyr(OBn)-Ser(OBn)-Trp-Gly-NHNH$_2$ Seq ID NO:31;
BnNHCO-His-Tyr(OBn)-Ser(OBn)-Trp-Gly-OMe Seq ID NO:32;
BnNHCO-His-Tyr(OBn)-Ser(OBn)-Trp-Gly Seq ID NO:33;
Cbz-His-Tyr(OBn)-Cys-Trp-D-Ala-NH$_2$;
Cbz-His-Tyr(OBn)-Cys-Trp-D-Ala-NHMe;
Cbz-His-Tyr(OBn)-Cys-Trp-D-Ala-NHEt;
Cbz-His-Tyr(OBn)-Cys-Trp-D-Ala-NHNH$_2$;
Cbz-His-Tyr(OBn)-Cys-Trp-D-Ala-OMe;
Cbz-His-Tyr(OBn)-Cys-Trp-D-Ala;
Cbz-His-Tyr(OBn)-Cys-Trp-Ala-NH$_2$ Seq ID NO:34;
Cbz-His-Tyr(OBn)-Cys-Trp-Ala-NHMe Seq ID NO:35;
Cbz-His-Tyr(OBn)-Cys-Trp-Ala-NHEt Seq ID NO:36;
Cbz-His-Tyr(OBn)-Cys-Trp-Ala-NHNH$_2$ Seq ID NO:37;
Cbz-His-Tyr(OBn)-Cys-Trp-Ala-OMe Seq ID NO:38;
Cbz-His-Tyr(OBn)-Cys-Trp-Ala Seq ID NO:39;
Cbz-His-Tyr(OBn)-Cys-Trp-Gly-NH$_2$ Seq ID NO:40;
Cbz-His-Tyr(OBn)-Cys-Trp-Gly-NHMe Seq ID NO:41;
Cbz-His-Tyr(OBn)-Cys-Trp-Gly-NHEt Seq ID NO:42;
Cbz-His-Tyr(OBn)-Cys-Trp-Gly-NHNH$_2$ Seq ID NO:43;
Cbz-His-Tyr(OBn)-Cys-Trp-Gly-OMe Seq ID NO:44;
Cbz-His-Tyr(OBn)-Cys-Trp-Gly Seq ID NO:45;
BnNHCO-His-Tyr(OBn)-Cys-Trp-D-Ala-NH$_2$;
BnNHCO-His-Tyr(OBn)-Cys-Trp-D-Ala-NHMe;
BnNHCO-His-Tyr(OBn)-Cys-Trp-D-Ala-NHEt;
BnNHCO-His-Tyr(OBn)-Cys-Trp-D-Ala-NHNH$_2$;
BnNHCO-His-Tyr(OBn)-Cys-Trp-D-Ala-OMe;
BnNHCO-His-Tyr(OBn)-Cys-Trp-D-Ala;
BnNHCO-His-Tyr(OBn)-Cys-Trp-Ala-NH$_2$ Seq ID NO:46;
BnNHCO-His-Tyr(OBn)-Cys-Trp-Ala-NHMe Seq ID NO:47;
BnNHCO-His-Tyr(OBn)-Cys-Trp-Ala-NHEt Seq ID NO:48;
BnNHCO-His-Tyr(OBn)-Cys-Trp-Ala-NHNH$_2$ Seq ID NO:49;
BnNHCO-His-Tyr(OBn)-Cys-Trp-Ala-OMe Seq ID NO:50;
BnNHCO-His-Tyr(OBn)-Cys-Trp-Ala Seq ID NO:51;
BnNHCO-His-Tyr(OBn)-Cys-Trp-Gly-NH$_2$ Seq ID NO:52;
BnNHCO-His-Tyr(OBn)-Cys-Trp-Gly-NHMe Seq ID NO:53;
BnNHCO-His-Tyr(OBn)-Cys-Trp-Gly-NHEt Seq ID NO:54;
BnNHCO-His-Tyr(OBn)-Cys-Trp-Gly-NHNH$_2$ Seq ID NO:55;
BnNHCO-His-Tyr(OBn)-Cys-Trp-Gly-OMe Seq ID NO:56;
BnNHCO-His-Tyr(OBn)-Cys-Trp-Gly Seq ID NO:57;
Cbz-Cys-Tyr(OBn)-Ser(OBn)-Trp-DAla-NH$_2$;
Cbz-His-Tyr(OPO$_3$H$_2$)-Ser(OBn)-Trp-DAla-NH$_2$;
Cbz-His-p(CH$_2$PO$_3$H$_2$)Phe-Ser(OBn)-Trp-DAla-NH$_2$;
Cbz-His-p(CH$_2$PO$_3$Et$_2$)Phe-Ser(OBn)-Trp-DAla-NH$_2$;
Cbz-His-p(CF$_2$PO$_3$H$_2$)Phe-Ser(OBn)-Trp-DAla-NH$_2$;
Cbz-His-Glu-Ser(OBn)-Trp-DAla-NH$_2$;
Cbz-His-Asp-Ser(OBn)-Trp-DAla-NH$_2$;

Cbz-His-Tyr(OBn)-Ser(OPO₃H₂)-Trp-DAla-NH₂;
Cbz-His-Tyr(OPO₃H₂)-Cys-Trp-DAla-NH₂; and
Cbz-His-Tyr(OPO₃H₂)-Ser(OBn)-Trp-NH₂ Seq ID NO:58.

GENERAL METHODS FOR THE PREPARATION, EVALUATION AND USE OF COMPOUNDS OF FORMULA I

The compounds of Formula I may be prepared by solid phase peptide synthesis on a peptide synthesizer, for example, an Applied Biosystems 430A peptide synthesizer using activated esters or anhydrides of Boc or Fmoc protected amino acids, acid chlorides, isocyanates, isothiocyanates, etc. on PAM, MBHA, or NH₂-Rink resins with solution phase modifications to the carboxyl terminus as appropriate. Methodology for the solid phase synthesis of peptides is widely known to those skilled in the art thereof (see, for example: J. M. Stewart and J. D. Young in *Solid Phase Peptide Synthesis;* Pierce Chemical Co.; Rockford, Ill. (1984); G. B. Fields and R. L. Noble, *Int. J. Peptide Protein Res.* 35, 161–214 (1990)). Additionally, the compounds of Formula I may also be prepared by conventional solution peptide synthesis, substituting amines, acid chlorides, isocyanates, etc. for amino acid derivatives where appropriate. Methods for solution phase synthesis of peptides are widely known to those skilled in the art (see, for example, M. Bodanszky, *Principles of Peptide Synthesis*, Springer-Verlag (1984)). For both of the synthetic methods described above appropriate consideration is given to protection and deprotection of reactive functional groups and to the sequence of synthetic steps. Knowledge of the use of common protecting groups and strategy for the assembly of complex organic molecules are within the usual realm of expertise of a practitioner of the art of organic chemistry (see, for example: T. W. Greene and P. G. M Wuts, *Protective Groups in Organic Chemistry*, John Wiley and Sons (1991); E. J. Corey and X.-M. Cheng, *The Logic of Chemical Synthesis*, John Wiley and Sons (1989)).

The homogeneity and composition of the resulting compounds is verified by RP-HPLC, capillary electrophoresis, thin layer chromatography (TLC), proton nuclear magnetic resonance spectrometry (NMR), amino acid analysis, chemical ionization mass spectrometry (CI-MS), fast atom bombardment mass spectrometry (FAB-MS) and electrospray mass spectrometry (ES-MS).

The compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydroiodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine (see, for example, S. M. Berge, et al., "Pharmaceutical Salts," *Journal of Pharmaceutical Science* 66, 1–19 (1977)).

The acid addition salts of said basic compounds are prepared by contacting the free base form with a sufficient amount of the desired acid to produce the salt in the conventional manner. Preferably a compound of Formula I can be converted to an acidic salt by treating with an aqueous solution of the desired acid, such that the resulting pH is less than 4. The solution can be passed through a C18 cartridge to absorb the compound, washed with copious amounts of water, the compound eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner or as above. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, S. M. Berge, et al., "Pharmaceutical Salts", *Journal of Pharmaceutical Science* 66, 1–19 (1977)).

The base addition salts of said acidic compounds are prepared by contacting the free acid form with a sufficient amount of the desired base to produce the salt in the conventional manner. Preferably, a compound of Formula I can be converted to a base salt by treating with an aqueous solution of the desired base, such that the resulting pH is greater than 9. The solution can be passed through a C18 cartridge to absorb the compound, washed with copious amounts of water, the compound eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner or as above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention. Certain of the compounds of the present invention possess one or more chiral centers and each center may exist in the R(D) or S(L) configuration. The present invention includes all enantiomeric and epimeric forms as well as the appropriate mixtures thereof.

The PFT inhibitory activity of compounds of Formula I was assayed in 30 mM potassium phosphate buffer, pH 7.4, containing 7 mM DTT, 1.2 MM MgCl₂, 0.1 mM leupeptin, 0.1 mM pepstatin, and 0.2 mM phenylmethylsulfonyl fluoride. Assays were performed in 96 well plates (Wallec) and employed solutions composed of varying concentrations of a compound of Formula I in 100% DMSO. Upon addition of both substrates, radiolabeled farnesyl pyrophosphate ([1-$^3$H], specific activity 15–30 Ci/mmol, final concentration 0.12 µM) and (biotinyl)-Ahe-Tyr-Lys-Cys-Val-Ile-Met peptide (final concentration 0.1 µM), the Seq ID NO:59 enzyme reaction was started by addition of 40-fold purified rat brain farnesyl protein transferase. After incubation at 37° C for 30 minutes, the reaction was terminated by diluting the reaction 2.5-fold with a stop buffer containing 1.5M magnesium acetate, 0.2M $H_3PO_4$, 0.5% BSA, and strepavidin beads (Amersham) at a concentration of 1.3 mg/mL. After allowing the plate to settle for 30 minutes at room temperature, radioactivity was quantitated on a microBeta counter (model 1450, Wallec).

As shown below in Table I, compounds of Formula I show $IC_{50}$ values of 0.5 to 1000 nM in the assay discussed above and are thus valuable inhibitors of protein:farnesyl transferase enzyme which may be used in the medical treatment of tissue proliferative diseases, including cancer and restenosis.

TABLE I

SEQ ID NO: 10

| Peptide | $IC_{50}$ (µM) |
|---|---|
| Cbz—His—Tyr(OBn)—Ser(OBn)—Trp—DAla—NH$_2$ | 0.017 |
| Cbz—His—Tyr(OBn)—Ser(OBn)—Trp—DAla—NHEt | 0.230 |
| Cbz—His—Tyr(OBn)—Ser(OBn)—Trp—DAla—NHNH$_2$ | 0.062 |
| Cbz—His—Tyr(OBn)—Ser(OBn)—Trp—DAla—OMe | 0.019 |
| Cbz—His—Tyr(OBn)—Ser(OBn)—Trp—DAla—OH | 0.048 |
| Cbz—His—Tyr(OBn)—Ser(OBn)—Trp—Ala—NH$_2$ | 0.015 |
| Cbz—His—Tyr—Ser(OBn)—Trp—DAla—NH$_2$ | 0.040 |
| Cbz—His—Tyr(OBn)—Ser—Trp—DAla—NH$_2$ | 1.8 |
| Cbz—His—Phe—Ser(OBn)—Trp—DAla—NH$_2$ | 0.010 |
| Cbz—His—Tyr(OBn)—Ser(OBn)—Ala—DAla—NH$_2$ | 0.33 |
| Cbz—DHis—Tyr(OBn)—Ser(OBn)—Trp—DAla—NH$_2$ | 0.12 |
| Cbz—His—DTyr(OBn)—Ser(OBn)—Trp—DAla—NH$_2$ | 0.039 |
| Cbz—His—Tyr(OBn)—Ser(OBn)—Trp—OMe SEQ ID NO: 18 | 0.115 |
| Cbz—His—Tyr(OBn)—Ser(OBn)—Trp—NH$_2$ SEQ ID NO: 19 | 0.083 |
| Cbz—His—Tyr(OBn)—Ser(OBn)—DAla—OM2 | 0.142 |
| Cbz—His—Tyr(OBn)—Ser(OBn)—DAla—OH | 0.404 |
| Cbz—His—Tyr(OBn)—Cys—Trp—DAla—NH$_2$ | 0.004 |
| Cbz—His—Tyr(OPO$_3$H$_2$)—Ser(OBn)—Trp—DAla—NH$_2$ | 0.009 |

The compounds of the present invention can be prepared and administered in a wide variety of oral, rectal, and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5 or 10 to about 70 percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as inhibitors of PFT, the compounds utilized in the pharmaceutical methods of this invention are administered at the initial dosage of about 0.01 mg/kg to about 20 mg/kg daily. A daily dose range of about 0.01 mg/kg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the inventors' preferred methods for preparing the compounds of the invention. For added clarity, complex chemical names describing compounds of Formula I are followed by structural abbreviations, which are shown in braces, wherein the structural elements are as defined in the Table of Abbreviations above.

EXAMPLE 1

N-[N-[N-[N-[(Phenylmethoxy)carbonyl]-L-histidyl]-O-(phenylmethyl)-L-tyrosyl]-O-(phenylmethyl)-L-seryl]-D-alanine, methyl ester {Cbz-His-Tyr(OBn)-Ser(OBn)-D-Ala-OMe}

Step 1: Boc-Ser(OBn)-D-Ala-OMe

To a solution of Boc-Ser(OBn) (4.12 g, 13.95 mmol) in EtOAc (100 mL) at 0° C. was added HOBT (2.35 g, 15.35 mmol) and DCC (3.17 g, 15.35 mmol). D-Alanine methyl ester hydrochloride (1.95 g, 13.95 mmol) was added followed by $Et_3N$ (2.14 mL, 15.35 mmol). The mixture was allowed to warm to room temperature and stirred overnight. The mixture was filtered, and the filtrate was washed with saturated aqueous $NaHCO_3$, brine, dried ($MgSO_4$), and concentrated. Flash chromatography (40% EtOAc/hexane) gave 2.60 g of the title compound as a colorless oil; CI-MS 381 (m+1).

Step 2: Ser(OBn)-D-Ala-OMe.TFA

To a solution of Boc-Ser(OBn)-D-Ala-$CO_2$Me from Step 1 above (2.44 g, 6.41 mmol) in $CH_2Cl_2$ (10 mL) was added TFA (3 mL). The solution was stirred for 6 hours at room temperature, then concentrated. The residue was taken up in $CH_2Cl_2$ and reconcentrated. After trituration with ether, the title compound was obtained as a white solid, mp 109°–110° C.

Step 3: Boc-Tyr(OBn)-Ser(OBn)-D-Ala-OMe

To a solution of Boc-Tyr(OBn) (0.94 g, 2.54 mmol) in DMF (10 mL) at 0° C. was added HOBT (0.47 g, 3.04 mmol) and DCC (0.63 g, 3.04 mmol). Ser(OBn)-D-Ala-$CO_2$Me.TFA from Step 2 above (1.0 g, 2.54 mmol) was added followed by $Et_3N$ (0.42 mL, 3.04 mmol). The mixture was allowed to warm to room temperature and stirred overnight. The mixture was filtered, and the filtrate was diluted with $CHCl_3$, washed twice with saturated aqueous $NaHCO_3$, brine, dried ($MgSO_4$), and concentrated. Flash chromatography (50% EtOAc/hexane) gave 1.35 g of the title compound as a white solid, mp 132°–133° C.; CI-MS 634 (m+1).

Step 4: Tyr(OBn)-Ser(OBn)-D-Ala-OMe.TFA

Prepared according to Step 2 above, substituting Boc-Tyr(OBn)-Ser(OBn)-D-Ala-$CO_2$Me for Boc-Ser(OBn)-D-Ala-$CO_2$Me. The title compound was obtained as a white solid; CI-MS 534 (m+1).

Step 5: Cbz-His-Tyr(OBn)-Ser(OBn)-D-Ala-OMe

Prepared according to Step 3 above, by substituting Cbz-His for Boc-Tyr(OBn) and Tyr(OBn)-Ser(OBn)-D-Ala-$CO_2$Me.TFA for Ser(OBn)-D-Ala-$CO_2$Me.TFA. The title compound was obtained as a white solid, mp 188°–191° C.

Anal. Calc. for $C_{44}H_{48}N_6O_9 \cdot H_2O$: C, 64.22; H, 6.12; N, 10.21;

Found: C, 64.15; H, 5.99; N, 10.17.

EXAMPLE 2

N-[N-[N-[(Phenylmethoxy)carbonyl]-L-histidyl]-O-(phenylmethyl)-L-tyrosyl]-O-(phenylmethyl)-L-seryl]-D-alanine, monohydrochloride {Cbz-His-Tyr(OBn)-Ser(OBn)-D-Ala.HCl}

To a suspension of Cbz-His-Tyr(OBn)-Ser(OBn)-D-Ala-$CO_2$Me from Example 1 above (0.43 g, 0.53 mmol) in THF (10 mL) and MeOH (3 mL) at 0° C. was added 0.1N LiOH (5.9 mL). The mixture was stirred for 6 hours at 0° C. and then concentrated. Water was added and the pH was adjusted to 4–5 by the addition of 1N HCl. The mixture was filtered, and the precipitate was collected and dried to afford 0.37 g of the title compound as a white solid, mp 190°–197° C.; FAB-MS 791 (m+1).

EXAMPLE 3

N-[N-[N-[(Phenylmethoxy)carbonyl]-L-histidyl]-O-(phenylmethyl)-L-tyrosyl]-O-(phenylmethyl)-L-seryl]-L-tryptophan, methyl ester {Cbz-His-Tyr(OBn)-Ser(OBn)-Trp-OMe}

Step 1: Boc-Tyr(OBn)-Ser(OBn)-OMe Seq ID NO:18

To a solution of Boc-Tyr(OBn) (1.88 g, 6.50 mmol) in EtOAc (30 mL) at 0° C. was added HOBT hydrate (1.19 g, 7.80 mmol) followed by DCC (1.61 g, 7.80 mmol). A solution of Ser(OBn)-$CO_2$Me.TFA (2.1 g, 6.50 mmol) in EtOAc (20 mL) was added followed by $Et_3N$ (1.09 mL, 7.80 mmol). The mixture was allowed to warm to room temperature and stirred overnight. The mixture was filtered, diluted with EtOAc, and washed twice with saturated aqueous $NaHCO_3$, brine, dried over $MgSO_4$, and concentrated. Flash chromatography (40% EtOAc/hexane) gave 2.67 g (73%) of the title compound as a white solid, mp 81°–84° C.

Step 2: Boc-Tyr(OBn)-Ser(OBn)

Prepared according to Example 2, by substituting Boc-Tyr(OBn)-Ser(OBn)-$CO_2$Me for Cbz-His-Tyr(OBn)-Ser(OBn)-D-Ala-$CO_2$Me. The title compound was obtained as a white foam.

Step 3: Boc-Tyr(OBn)-Ser(OBn)-Trp-OMe

Prepared according to Example 1, Step 3, by substituting Boc-Tyr(OBn)-Ser(OBn) for Boc-Tyr(OBn) and Trp-$CO_2$Me.HCl for Ser(OBn)-D-Ala-$CO_2$Me.TFA. The title compound was obtained as a white foam; FAB-MS 750 (m+1).

Step 4: Tyr(OBn)-Ser(OBn)-Trp-OMe.TFA

Prepared according to Example 1, Step 2, by substituting Boc-Tyr(OBn)-Ser(OBn)-Trp-$CO_2$Me for Boc-Ser(OBn)-D-Ala-$CO_2$Me, and adding 2 equiv of thioanisole in addition to TFA. The title compound was obtained as white solid.

Step 5: Cbz-His-Tyr(OBn)-Ser(OBn)-Trp-OMe Seq ID NO:18

Prepared according to Example 1, Step 5, by substituting Tyr(OBn)-Ser(OBn)-Trp-$CO_2$Me.TFA for Tyr(OBn)-Ser(OBn)-D-Ala-$CO_2$Me.TFA. The title compound was obtained as a white foam; FAB-MS 920 (m+1).

EXAMPLE 4

$N_\alpha$-[N-[N-[N-[(Phenylmethoxy)carbonyl]-L-histidyl]-O-(phenylmethyl)-L-tyrosyl]-O-(phenylmethyl)-L-seryl]-L-tryptophyl]-D-alaninamide {Cbz-His-Tyr(OBn)-Ser(OBn)-Trp-D-Ala-$NH_2$}

Using an ABI model 431A solid phase peptide synthesizer, Fmoc-NH-Rink resin (0.25 mmol scale) was treated with 20% piperidine in NMP to afford $NH_2$-Rink resin. Sequential coupling of Fmoc-protected D-Ala, Trp, Ser(OBn) and Tyr(OBn) (DCC and HOBT in NMP) and Fmoc deprotection (20% piperidine in NMP) reactions were run using a fourfold excess of reagents in the coupling steps and traditional resin washing cycles to afford Tyr(OBn)-Ser(OBn)-Trp-D-Ala-CONH-Rink resin. This tetrapeptide resin was transferred to an uninstrumented reaction vessel and treated with a fourfold excess of Cbz-His, DCC and HOBT in DMF, shaking overnight at room temperature. After removal of excess reagents, the resulting substituted pentapeptide was cleaved from the resin by treatment with 50% TFA in DCM at room temperature for 2.5 hours. Evaporation of solvents, lyophilization and purification by reversed phase chromatography ($C_{18}$-column, eluted with a 20–70% gradient of MeCN in water (both solvents acidified with 0.1% TFA)) afforded Cbz-His-Tyr(OBn)-Ser(OBn)-Trp-D-Ala-$CONH_2$ as its TFA salt upon lyophilization. FAB-MS: 976 (m+1).

Using analogous methods the following most preferred compounds of Formula I with carboxamides at the C-terminus may be prepared:

Cbz-His-Tyr(OBn)-Ser(OBn)-Trp-Ala-$NH_2$, ES-MS 976 (m+1) Seq ID NO:5;

Cbz-His-Tyr(OBn)-Ser(OBn)-Trp-Gly-$NH_2$ Seq ID NO:11;

Cbz-His-Tyr-Ser(OBn)-Trp-D-Ala-$NH_2$, FAB-MS 886 (m+1);

Cbz-His-D-Tyr(OBn)-Ser(OBn)-Trp-D-Ala-$NH_2$, FAB-MS 976 (m+1);

Cbz-His-Phe-Ser(OBn)-Trp-D-Ala-$NH_2$, ES-MS 870 (m+1);

Cbz-His-Tyr(OBn)-Ser-Trp-D-Ala-$NH_2$, FAB-MS 886 (m+1);

Cbz-D-His-Tyr(OBn)-Ser(OBn)-Trp-D-Ala-$NH_2$, FAB-MS 976 (m+1);

Cbz-His-Tyr(OBn)-Ser(OBn)-Trp-$NH_2$, ES-MS 905 (m+1) Seq ID NO:19;

Cbz-His-Tyr(OBn)-Ser(OBn)-Ala-D-Ala-$NH_2$, ES-MS 861 (m+1);

Cbz-His-Phe-Ser(OBn)-Trp-Ala-$NH_2$; ES-MS 870 (m+1) Seq ID NO:17;

BnNHCO-His-Tyr(OBn)-Ser(OBn)-Trp-Gly-$NH_2$ Seq ID NO:28;

BnNHCO-His-Tyr(OBn)-Ser(OBn)-Trp-D-Ala-$NH_2$ Seq ID NO:22 ;

BnNHCO-His-Tyr(OBn)-Ser(OBn)-Trp-Ala-$NH_2$;

Cbz-His-Tyr($OPO_3H_2$)-Ser(OBn)-Trp-DAla-$NH_2$, ES-MS 966 (m+1);

Cbz-His-p($CH_2PO_3H_2$)Phe-Ser(OBn)-Trp-DAla-$NH_2$;

Cbz-His-p ($CH_2PO_3Et_2$) Phe-Ser(OBn)-Trp-DAla-$NH_2$, ES-MS 1021 (m+1);

Cbz-His-p($CF_2PO_3H_2$)Phe-Ser(OBn)-Trp-DAla-$NH_2$;

Cbz-His-Glu-Ser(OBn)-Trp-DAla-$NH_2$, ES-MS 852.3 (m+1);

Cbz-His-Asp-Ser(OBn)-Trp-DAla-$NH_2$, ES-MS 838.6 (m+1);

Cbz-His-Tyr(OBn)-Ser($OPO_3H_2$)-Trp-DAla-$NH_2$, FAB-MS 966.2 (m+1); and

Cbz-His-Tyr($OPO_3H_2$)-Ser(OBn)-Trp-$NH_2$ Seq ID NO:58, ES-MS 895.5 (m+1).

EXAMPLE 5

$N_\alpha$-[N-[N-[N-[(Phenylmethoxy)carbonyl]-L-histidyl]-O-(phenylmethyl)-L-tyrosyl]-L-cysteinyl-L-tryptophyl]-D-alaninamide {Cbz-His-Tyr(OBn)-Cys-Trp-D-Ala-$NH_2$}

Sequential coupling and deprotection of Fmoc-protected D-Ala, Trp, Cys(STr), Tyr(OBn) and Cbz-His by the solid phase method described in Example 4, followed by treatment with 60% TFA in DCM for 3.5 hours at room temperature gave crude Cbz-His-Tyr(OBn)-Cys-Trp-D-Ala-$CONH_2$ upon evaporation of solvents and lyophilization. Purification was accomplished by reversed phase chromatography on a $C_{18}$ column, eluted with a 25 to 75% gradient of MeCN in water (both solvents acidified with 0.1% TFA) to give the TFA salt of the title compound upon lyophilization. ES-MS: 902 (m+1).

Using analogous methods the following most preferred compounds of Formula I which contain Cys and a carboxamide at the C-terminus may be prepared:

Cbz-His-Tyr(OBn)-Cys-Trp-Ala-$NH_2$ Seq ID NO:34;

Cbz-His-Tyr(OBn)-Cys-Trp-Gly-$NH_2$ Seq ID NO:40;

BnNHCO-His-Tyr(OBn)-Cys-Trp-D-Ala-$NH_2$;

BnNHCO-His-Tyr(OBn)-Cys-Trp-Ala-$NH_2$ Seq ID NO:46;

BnNHCO-His-Tyr(OBn)-Cys-Trp-Gly-$NH_2$ Seq ID NO:52;

Cbz-Cys-Tyr(OBn)-Ser(OBn)-Trp-DAla-$NH_2$, FAB-MS 942.6 (m+1); and

Cbz-His-Tyr($OPO_3H_2$)-Cys-Trp-DAla-$NH_2$.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

---

What is claimed is:

1. A compound of the Formula I:

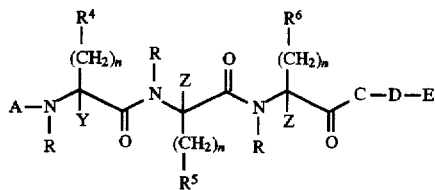

wherein each n is independently 1 or 2;

A is carboxybenzyloxy;

each R, Y, Z, R⁴, or R⁷ is independently hydrogen or methyl;

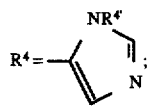

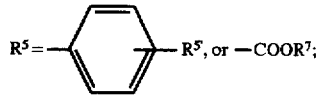

$R^{5'}$ is hydrogen, —OH, —$(CH_2)_m$-phenyl, —O$(CH_2)_m$phenyl, —OPO$_3R^{5''}_2$, or —CH$_2$PO$_3R^{5''}_2$;

$R^{5''}$ is hydrogen or $C_1$–$C_6$ alkyl;

m is 0, 1 or 2;

$R^6$ is —$OR^{6'}$ or —SH;

$R^{6'}$ is hydrogen, benzyl or —PO$_3R^{5''}_2$;

C is Ala, Phe, Tyr, Trp, Trp(Me), or Trp(CHO);

D is Gly, Ala, or absent;

E is —NHNH$_2$, —NHR¹⁰, or —OR¹⁰; and

R¹⁰ is hydrogen, or $C_1$–$C_6$ alkyl; or a stereoisomer or a pharmaceutically acceptable salt thereof.

2. A compound according to claim 1 which is a compound of Formula II:

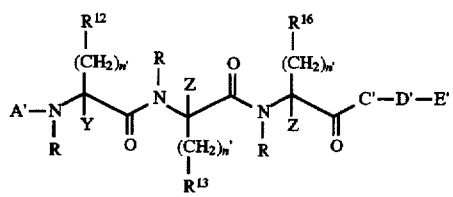

wherein each n' is independently 1 or 2;

A is carboxybenzyloxy;

each R, Y, Z, or R¹⁵ is independently hydrogen or methyl;

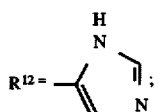

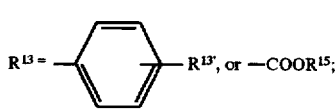

$R^{13'}$ is hydrogen, —OH, —Obenzyl, or —OPO$_3H_2$;

$R^{16}$ is —OH, —Obenzyl, or —SH;

C' is Ala, Trp, Trp(Me) or Trp(CHO);

D' is Gly, Ala, or absent; and

E' is —OMe, —NH$_2$, or —NHNH$_2$; or a stereoisomer or a pharmaceutically acceptable salt thereof.

3. A compound according to claim 1 wherein each R is hydrogen and n is 1 or 2.

4. A compound according to claim 1 wherein

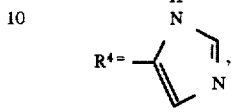

and Y and Z are hydrogen.

5. A compound according to claim 1 wherein $R^5$ is

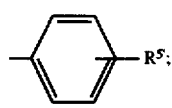

and $R^{5'}$ is hydrogen, —OH or —Obenzyl.

6. A compound according to claim 1 wherein $R^6$ is Obenzyl, —OH, or —SH.

7. A compound according to claim 1 wherein C is Trp or Ala.

8. A compound according to claim 7 wherein D is Gly, Ala, or absent.

9. A compound according to claim 1 wherein E is —NH$_2$, —OH, —OMe, —NHEt, —NHNH$_2$ or —NHMe.

10. The compounds:

Cbz-His-Tyr(OBn)-Ser(OBn)-Trp-D-Ala-NH$_2$;

Cbz-His-Tyr(OPO$_3H_2$)-Ser(OBn)-Trp-D-Ala-NH$_2$;

Cbz-His-p(CH$_2$PO$_3H_2$)Phe-Ser(OBn)-Trp-D-Ala-NH$_2$;

Cbz-His-p(CH$_2$PO$_3$Et$_2$)Phe-Ser(OBn)-Trp-D-Ala-NH$_2$;

Cbz-His-p(CF$_2$PO$_3H_2$)Phe-Ser(OBn)-Trp-D-Ala-NH$_2$;

Cbz-His-Glu-Ser(OBn)-Trp-D-Ala-NH$_2$;

Cbz-His-Asp-Ser(OBn)-Trp-D-Ala-NH$_2$;

Cbz-His-Tyr(OBn)-Ser(OPO$_3H_2$)-Trp-D-Ala-NH$_2$;

Cbz-His-Tyr(OPO$_3H_2$)-Cys-Trp-D-Ala-NH$_2$; and

Cbz-His-Tyr(OPO$_3H_2$)-Ser(OBn)-Trp-NH$_2$ Seq ID No: 58.

11. The compounds:

Cbz-His-Tyr(OBn)-Ser(OBn)-Trp-D-Ala-NHMe;

Cbz-His-Tyr(OBn)-Ser(OBn)-Trp-D-Ala-NHEt;

Cbz-His-Tyr(OBn)-Ser(OBn)-Trp-D-Ala-NHNH$_2$;

Cbz-His-Tyr(OBn)-Ser(OBn)-Trp-D-Ala-OMe;

Cbz-His-Tyr(OBn)-Ser(OBn)-Trp-D-Ala;

Cbz-His-Tyr(OBn)-Ser(OBn)-Trp-Ala-NH$_2$ Seq ID No: 5;

Cbz-His-Tyr(OBn)-Ser(OBn)-Trp-Ala-NHMe Seq ID No: 6;

Cbz-His-Tyr(OBn)-Ser(OBn)-Trp-Ala-NHEt Seq ID No: 7;

Cbz-His-Tyr(OBn)-Ser(OBn)-Trp-Ala-NHNH$_2$ Seq ID No: 8;

Cbz-His-Tyr(OBn)-Ser(OBn)-Trp-Ala-OMe Seq ID No: 9;

Cbz-His-Tyr(OBn)-Ser(OBn)-Trp-Ala Seq ID No: 10;

Cbz-His-Tyr(OBn)-Ser(OBn)-Trp-Gly-NH$_2$ Seq ID No: 11;

Cbz-His-Tyr(OBn)-Ser(OBn)-Trp-Gly-NHMe Seq ID No: 12;

Cbz-His-Tyr(OBn)-Ser(OBn)-Trp-Gly-NHEt Seq ID No: 13;

Cbz-His-Tyr(OBn)-Ser(OBn)-Trp-Gly-NHNH$_2$ Seq ID No: 14;

Cbz-His-Tyr(OBn)-Ser(OBn)-Trp-Gly-OMe Seq ID No: 15; and

Cbz-His-Tyr(OBn)-Ser(OBn)-Trp-Gly Seq ID No: 16.

12. The compounds:

Cbz-His-Tyr-Ser(OBn)-Trp-D-Ala-NH$_2$;

Cbz-His-Tyr(OBn)-Ser-Trp-D-Ala-NH$_2$;

Cbz-His-Phe-Ser(OBn)-Trp-D-Ala-NH$_2$;

Cbz-His-Phe-Ser(OBn)-Trp-Ala-NH$_2$ Seq ID No: 17;

Cbz-His-Tyr(OBn)-Ser(OBn)-Ala-D-Ala-NH$_2$;

Cbz-D-His-Tyr(OBn)-Ser(OBn)-Trp-D-Ala-NH$_2$; and

Cbz-His-D-Tyr(OBn)-Ser(OBn)-Trp-D-Ala-NH$_2$.

13. The compounds:

Cbz-His-Tyr(OBn)-Ser(OBn)-Trp-OMe Seq ID No: 18;

Cbz-His-Tyr(OBn)-Ser(OBn)-Trp-NH$_2$ Seq ID No: 19;

Cbz-His-Tyr(OBn)-Ser(OBn)-D-Ala-OMe;

Cbz-His-Tyr(OBn)-Ser(OBn)-D-Ala;

Cbz-D-His-Tyr(OBn)-Ser(OBn)-Trp-OMe;

Cbz-His-D-Tyr(OBn)-Ser(OBn)-Trp-OMe;

Cbz-His-Tyr(OBn)-Cys-Trp-NH$_2$ Seq ID No: 20; and

BnNHCO-His-Tyr(OBn)-Cys-Trp-NH$_2$ Seq ID No: 21.

14. The compounds:

Cbz-His-Tyr(OBn)-Cys-Trp-D-Ala-NH$_2$;

Cbz-His-Tyr(OBn)-Cys-Trp-D-Ala-NHMe;

Cbz-His-Tyr(OBn)-Cys-Trp-D-Ala-NHEt;

Cbz-His-Tyr(OBn)-Cys-Trp-D-Ala-NHNH$_2$;

Cbz-His-Tyr(OBn)-Cys-Trp-D-Ala-OMe;

Cbz-His-Tyr(OBn)-Cys-Trp-D-Ala;

Cbz-His-Tyr(OBn)-Cys-Trp-Ala-NH$_2$ Seq ID No: 34;

Cbz-His-Tyr(OBn)-Cys-Trp-Ala-NHMe Seq ID No: 35;

Cbz-His-Tyr(OBn)-Cys-Trp-Ala-NHEt Seq ID No: 36;

Cbz-His-Tyr(OBn)-Cys-Trp-Ala-NHNH$_2$ Seq ID No: 37;

Cbz-His-Tyr(OBn)-Cys-Trp-Ala-OMe Seq ID No: 38;

Cbz-His-Tyr(OBn)-Cys-Trp-Ala Seq ID No: 39;

Cbz-His-Tyr(OBn)-Cys-Trp-Gly-NH$_2$ Seq ID No: 40;

Cbz-His-Tyr(OBn)-Cys-Trp-Gly-NHMe Seq ID No: 41;

Cbz-His-Tyr(OBn)-Cys-Trp-Gly-NHEt Seq ID No: 42;

Cbz-His-Tyr(OBn)-Cys-Trp-Gly-NHNH$_2$ Seq ID No: 43;

Cbz-His-Tyr(OBn)-Cys-Trp-Gly-OMe Seq ID No: 44; and

Cbz-His-Tyr(OBn)-Cys-Trp-Gly Seq ID No: 45.

15. A pharmaceutical composition comprising a therapeutically effective amount of a compound of Formula I

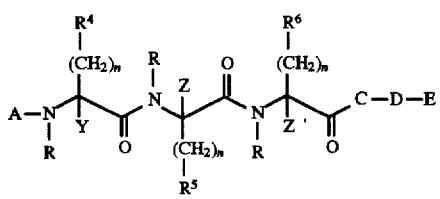

wherein each n is independently 1 or 2;

A is carboxybenzyloxy;

each R, Y, Z, R$^4$, or R$^7$ is independently hydrogen or methyl;

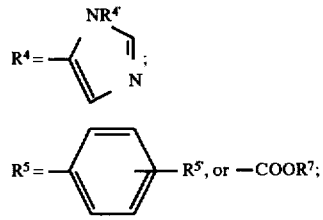

$R^5$ is hydrogen, —OH, —(CH$_2$)$_m$-phenyl, —O(CH$_2$)$_m$phenyl, —OPO$_3$R$^{5"}_2$, or —CH$_2$PO$_3$R$^{5"}_2$;

$R^{5"}$ is hydrogen or C$_1$-C$_6$ alkyl;

m is 0, 1 or 2;

$R^6$ is —OR$^{6'}$ or —SH;

$R^{6'}$ is hydrogen, benzyl or —PO$_3$R$^{5"}_2$;

C is Ala, Phe, Tyr, Trp, Trp(Me), or Trp(CHO);

D is Gly, Ala, or absent;

E is —NHNH$_2$, —NHR$^{10}$, or —OR$^{10}$; and

R$^{10}$ is hydrogen, or C$_1$-C$_6$ alkyl; or a stereoisomer or a pharmaceutically acceptable salt thereof, in admixture with a pharmaceutically acceptable excipient, diluent, or carrier.

16. A method of treating ras-related cancer comprising administering to a mammal suffering therefrom a therapeutically effective amount of a compound of Formula I

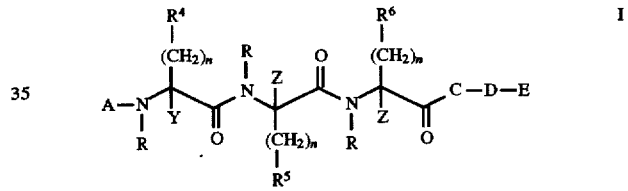

wherein each n is independently 1 or 2;

A is carboxybenzyloxy;

each R, Y, Z, R$^4$, or R$^7$ is independently hydrogen or methyl;

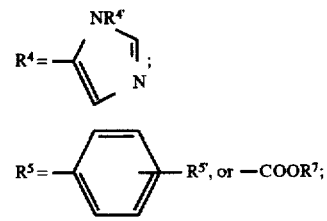

$R^5$ is hydrogen, —OH, —(CH$_2$)$_m$-phenyl, —O(CH$_2$)$_m$phenyl, —OPO$_3$R$^{5"}_2$, or —CH$_2$PO$_3$R$^{5"}_2$;

$R^{5"}$ is hydrogen or C$_1$-C$_6$ alkyl;

m is 0, 1 or 2;

$R^6$ is —OR$^{6'}$ or —SH;

$R^{6'}$ is hydrogen, benzyl or —PO$_3$R$^{5"}_2$;

C is Ala, Phe, Tyr, Trp, Trp(Me), or Trp(CHO);

D is Gly, Ala, or absent;

E is —NHNH$_2$, —NHR$^{10}$, or —OR$^{10}$; and

R$^{10}$ is hydrogen, or C$_1$-C$_6$ alkyl, or a stereoisomer or a pharmaceutically acceptable salt thereof.

17. A pharmaceutical composition comprising a therapeutically effective amount of a compound of Formula II $$\text{A'}-\underset{R}{\overset{R^{12}}{\underset{|}{\text{N}}}}-\underset{Y}{\overset{(CH_2)_{n'}}{\underset{|}{\text{C}}}}-\underset{R}{\overset{R}{\underset{|}{\text{N}}}}-\underset{Z}{\overset{(CH_2)_{n'}}{\underset{|}{\text{C}}}}-\underset{R}{\overset{R}{\underset{|}{\text{N}}}}-\underset{Z}{\overset{(CH_2)_{n'}}{\underset{|}{\text{C}}}}-\text{C'}-\text{D'}-\text{E'}$$

II wherein each n' is independently 1 or 2;

A' is carboxybenzyloxy;

each R, Y, Z, or $R^{15}$ is independently hydrogen or methyl;

$R^{12} = $ (imidazolyl structure);

$R^{13} = $ (phenyl with $R^{13'}$), or $-COOR^{15}$;

$R^{13'}$ is hydrogen, —OH, —Obenzyl, or —OPO$_3$H$_2$;

$R^{16}$ is —OH, —Obenzyl, or —SH;

C' is Ala, Trp, Trp(Me) or Trp(CHO);

D' is Gly, Ala, or absent; and

E' is —OMe, —NH$_2$, or —NHNH$_2$; or a stereoisomer or a pharmaceutically acceptable salt thereof, in admixture with a pharmaceuitcally acceptable excipient, diluent, or carrier.

18. A method of treating ras-related cancer comprising administering to a mammal suffering therefrom a therapeutically effective amount of a compound of Formula II $$\text{A'}-\underset{R}{\overset{R^{12}}{\underset{|}{\text{N}}}}-\underset{Y}{\overset{(CH_2)_{n'}}{\underset{|}{\text{C}}}}-\underset{R}{\overset{R}{\underset{|}{\text{N}}}}-\underset{Z}{\overset{(CH_2)_{n'}}{\underset{|}{\text{C}}}}-\underset{R}{\overset{R}{\underset{|}{\text{N}}}}-\underset{Z}{\overset{(CH_2)_{n'}}{\underset{|}{\text{C}}}}-\text{C'}-\text{D'}-\text{E'}$$

II wherein each n' is independently 1 or 2;

A' is carboxybenzyloxy;

each R, Y, Z, or $R^{15}$ is independently hydrogen or methyl;

$R^{12} = $ (imidazolyl structure);

$R^{13} = $ (phenyl with $R^{13'}$), or $-COOR^{15}$;

$R^{13'}$ is hydrogen, —OH, —Obenzyl, or —OPO$_3$H$_2$;

$R^{16}$ is —OH, —Obenzyl, or —SH;

C' is Ala, Trp, Trp(Me) or Trp(CHO);

D' is Gly, Ala, or absent; and

E' is —OMe, —NH$_2$, or —NHNH$_2$; or a stereoisomer or a pharmaceutically acceptable salt thereof.

19. A pharmaceutical composition comprising a therapeutically effective amount of a compound selected from the group consisting of Cbz-His-Tyr(OBn)-Ser(OBn)-Trp-D-Ala-NH$_2$;
Cbz-His-Tyr(OPO$_3$H$_2$)-Ser(OBn)-Trp-D-Ala-NH$_2$;
Cbz-His-p(CH$_2$PO$_3$H$_2$)Phe-Ser(OBn)-Trp-D-Ala-NH$_2$;
Cbz-His-p(CH$_2$PO$_3$Et$_2$)Phe-Ser(OBn)-Trp-D-Ala-NH$_2$;
Cbz-His-p(CF$_2$PO$_3$H$_2$)Phe-Ser(OBn)-Trp-D-Ala-NH$_2$;
Cbz-His-Glu-Ser(OBn)-Trp-D-Ala-NH$_2$;
Cbz-His-Asp-Ser(OBn)-Trp-D-Ala-NH$_2$;
Cbz-His-Tyr(OBn)-Ser(OPO$_3$H$_2$)-Trp-D-Ala-NH$_2$;
Cbz-His-Tyr(OPO$_3$H$_2$)-Cys-Trp-D-Ala-NH$_2$; and
Cbz-His-Tyr(OPO$_3$H$_2$)-Ser(OBn)-Trp-NH$_2$ Seq ID No: 58, in admixture with a pharmaceutically acceptable excipient, diluent, or carrier.

20. A method of treating ras-related cancer comprising administering to a mammal suffering therefrom a therapeutically effective amount of a compound selected from the group consisting of Cbz-His-Tyr(OBn)-Ser(OBn)-Trp-D-Ala-NH$_2$;
Cbz-His-Tyr(OPO$_3$H$_2$)-Ser(OBn)-Trp-D-Ala-NH$_2$;
Cbz-His-p(CH$_2$PO$_3$H$_2$)Phe-Ser(OBn)-Trp-D-Ala-NH$_2$;
Cbz-His-p(CH$_2$PO$_3$Et$_2$)Phe-Ser(OBn)-Trp-D-Ala-NH$_2$;
Cbz-His-p(CF$_2$PO$_3$H$_2$)Phe-Ser(OBn)-Trp-D-Ala-NH$_2$;
Cbz-His-Glu-Ser(OBn)-Trp-D-Ala-NH$_2$;
Cbz-His-Asp-Ser(OBn)-Trp-D-Ala-NH$_2$;
Cbz-His-Tyr(OBn)-Ser(OPO$_3$H$_2$)-Trp-D-Ala-NH$_2$;
Cbz-His-Tyr(OPO$_3$H$_2$)-Cys-Trp-D-Ala-NH$_2$; and
Cbz-His-Tyr(OPO$_3$H$_2$)-Ser(OBn)-Trp-NH$_2$ Seq ID No: 58.

21. A pharmaceutical composition comprising a therapeutically effective amount of a compound selected from the group consisting of Cbz-His-Tyr(OBn)-Ser(OBn)-Trp-D-Ala-NHMe;
Cbz-His-Tyr(OBn)-Ser(OBn)-Trp-D-Ala-NHEt;
Cbz-His-Tyr(OBn)-Ser(OBn)-Trp-D-Ala-NHNH$_2$;
Cbz-His-Tyr(OBn)-Ser(OBn)-Trp-D-Ala-OMe;
Cbz-His-Tyr(OBn)-Ser(OBn)-Trp-D-Ala;
Cbz-His-Tyr(OBn)-Ser(OBn)-Trp-Ala-NH$_2$ Seq ID No: 5;
Cbz-His-Tyr(OBn)-Ser(OBn)-Trp-Ala-NHMe Seq ID No: 6;
Cbz-His-Tyr(OBn)-Ser(OBn)-Trp-Ala-NHEt Seq ID No: 7;
Cbz-His-Tyr(OBn)-Ser(OBn)-Trp-Ala-NHNH$_2$ Seq ID No: 8;
Cbz-His-Tyr(OBn)-Ser(OBn)-Trp-Ala-OMe Seq ID No: 9;
Cbz-His-Tyr(OBn)-Ser(OBn)-Trp-Ala Seq ID No: 10;
Cbz-His-Tyr(OBn)-Ser(OBn)-Trp-Gly-NH$_2$ Seq ID No: 11;
Cbz-His-Tyr(OBn)-Ser(OBn)-Trp-Gly-NHMe Seq ID No: 12;
Cbz-His-Tyr(OBn)-Ser(OBn)-Trp-Gly-NHEt Seq ID No: 13;
Cbz-His-Tyr(OBn)-Ser(OBn)-Trp-Gly-NHNH$_2$ Seq ID No: 14;
Cbz-His-Tyr(OBn)-Ser(OBn)-Trp-Gly-OMe Seq ID No: 15; and Cbz-His-Tyr(OBn)-Ser(OBn)-Trp-Gly Seq ID No: 16,
in admixture with a pharmaceutically acceptable excipient, diluent, or carrier.

22. A method of treating ras-related cancer comprising administering to a mammal suffering therefrom a therapeutically effective amount of a compound selected from the group consisting of Cbz-His-Tyr(OBn)-Ser(OBn)-Trp-D-Ala-NHMe;
Cbz-His-Tyr(OBn)-Ser(OBn)-Trp-D-Ala-NHEt;
Cbz-His-Tyr(OBn)-Ser(OBn)-Trp-D-Ala-NHNH$_2$;
Cbz-His-Tyr(OBn)-Ser(OBn)-Trp-D-Ala-OMe;
Cbz-His-Tyr(OBn)-Ser(OBn)-Trp-D-Ala;
Cbz-His-Tyr(OBn)-Ser(OBn)-Trp-Ala-NH$_2$ Seq ID No: 5;
Cbz-His-Tyr(OBn)-Ser(OBn)-Trp-Ala-NHMe Seq ID No: 6;
Cbz-His-Tyr(OBn)-Ser(OBn)-Trp-Ala-NHEt Seq ID No: 7;
Cbz-His-Tyr(OBn)-Ser(OBn)-Trp-Ala-NHNH$_2$ Seq ID No: 8;
Cbz-His-Tyr(OBn)-Ser(OBn)-Trp-Ala-OMe Seq ID No: 9;
Cbz-His-Tyr(OBn)-Ser(OBn)-Trp-Ala Seq ID No: 10;
Cbz-His-Tyr(OBn)-Ser(OBn)-Trp-Gly-NH$_2$ Seq ID No: 11;
Cbz-His-Tyr(OBn)-Ser(OBn)-Trp-Gly-NHMe Seq ID No: 12;
Cbz-His-Tyr(OBn)-Ser(OBn)-Trp-Gly-NHEt Seq ID No: 13;
Cbz-His-Tyr(OBn)-Ser(OBn)-Trp-Gly-NHNH$_2$ Seq ID No: 14;
Cbz-His-Tyr(OBn)-Ser(OBn)-Trp-Gly-OMe Seq ID No: 15; and
Cbz-His-Tyr(OBn)-Ser(OBn)-Trp-Gly Seq ID No: 16.

23. A pharmaceutical composition comprising a therapeutically effective amount of a compound selected from the group consisting of Cbz-His-Tyr-Ser(OBn)-Trp-D-Ala-NH$_2$;
Cbz-His-Tyr(OBn)-Ser-Trp-D-Ala-NH$_2$;
Cbz-His-Phe-Ser(OBn)-Trp-D-Ala-NH$_2$;
Cbz-His-Phe-Ser(OBn)-Trp-Ala-NH$_2$ Seq ID No: 17;
Cbz-His-Tyr(OBn)-Ser(OBn)-Ala-D-Ala-NH$_2$;
Cbz-D-His-Tyr(OBn)-Ser(OBn)-Trp-D-Ala-NH$_2$; and
Cbz-His-D-Tyr(OBn)-Ser(OBn)-Trp-D-Ala-NH$_2$, in admixture with a pharmaceutically acceptable excipeint, diluent, or carrier.

24. A method of treating ras-related cancer comprising administering to a mammal suffering therefrom a therapeutically effective amount of a compound selected from the group consisting of Cbz-His-Tyr-Ser(OBn)-Trp-D-Ala-NH$_2$;
Cbz-His-Tyr(OBn)-Ser-Trp-D-Ala-NH$_2$;
Cbz-His-Phe-Ser(OBn)-Trp-D-Ala-NH$_2$;
Cbz-His-Phe-Ser(OBn)-Trp-Ala-NH$_2$ Seq ID No: 17;
Cbz-His-Tyr(OBn)-Ser(OBn)-Ala-D-Ala-NH$_2$;
Cbz-D-His-Tyr(OBn)-Ser(OBn)-Trp-D-Ala-NH$_2$; and
Cbz-His-D-Tyr(OBn)-Ser(OBn)-Trp-D-Ala-NH$_2$.

25. A pharmaceutical composition comprising a therapeutically effective amount of a compound selected from the group consisting of Cbz-His-Tyr(OBn)-Ser(OBn)-Trp-OMe Seq ID No: 18;
Cbz-His-Tyr(OBn)-Ser(OBn)-Trp-NH$_2$ Seq ID No: 19;
Cbz-His-Tyr(OBn)-Ser(OBn)-D-Ala-OMe;
Cbz-His-Tyr(OBn)-Ser(OBn)-D-Ala;
Cbz-D-His-Tyr(OBn)-Ser(OBn)-Trp-OMe;
Cbz-His-D-Tyr(OBn)-Ser(OBn)-Trp-OMe;
Cbz-His-Tyr(OBn)-Cys-Trp-NH$_2$ Seq ID No: 20; and
BnNHCO-His-Tyr(OBn)-Cys-Trp-NH$_2$ Seq ID No: 21,
in admixture with a pharmaceutically acceptable excipient, diluent, or carrier.

26. A method of treating ras-related cancer comprising administering to a mammal suffering therefrom a therapeutically effective amount of a compound selected from the group consisting of Cbz-His-Tyr(OBn)-Ser(OBn)-Trp-OMe Seq ID No: 18;
Cbz-His-Tyr(OBn)-Ser(OBn)-Trp-NH$_2$ Seq ID No: 19;
Cbz-His-Tyr(OBn)-Ser(OBn)-D-Ala-OMe;
Cbz-His-Tyr(OBn)-Ser(OBn)-D-Ala;
Cbz-D-His-Tyr(OBn)-Ser(OBn)-Trp-OMe;
Cbz-His-D-Tyr(OBn)-Ser(OBn)-Trp-OMe;
Cbz-His-Tyr(OBn)-Cys-Trp-NH$_2$ Seq ID No: 20; and
BnNHCO-His-Tyr(OBn)-Cys-Trp-NH$_2$ Seq ID No: 21.

27. A pharmaceutical composition comprising a therapeutically effective amount of a compound selected from the group consisting of Cbz-His-Tyr(OBn)-Cys-Trp-D-Ala-NH$_2$;
Cbz-His-Tyr(OBn)-Cys-Trp-D-Ala-NHMe;
Cbz-His-Tyr(OBn)-Cys-Trp-D-Ala-NHEt;
Cbz-His-Tyr(OBn)-Cys-Trp-D-Ala-NHNH$_2$;
Cbz-His-Tyr(OBn)-Cys-Trp-D-Ala-OMe;
Cbz-His-Tyr(OBn)-Cys-Trp-D-Ala;
Cbz-His-Tyr(OBn)-Cys-Trp-Ala-NH$_2$ Seq ID No: 34;
Cbz-His-Tyr(OBn)-Cys-Trp-Ala-NHMe Seq ID No: 35;
Cbz-His-Tyr(OBn)-Cys-Trp-Ala-NHEt Seq ID No: 36;
Cbz-His-Tyr(OBn)-Cys-Trp-Ala-NHNH$_2$ Seq ID No: 37;
Cbz-His-Tyr(OBn)-Cys-Trp-Ala-OMe Seq ID No: 38;
Cbz-His-Tyr(OBn)-Cys-Trp-Ala Seq ID No: 39;
Cbz-His-Tyr(OBn)-Cys-Trp-Gly-NH$_2$ Seq ID No: 40;
Cbz-His-Tyr(OBn)-Cys-Trp-Gly-NHMe Seq ID No: 41;
Cbz-His-Tyr(OBn)-Cys-Trp-Gly-NHEt Seq ID No: 42;
Cbz-His-Tyr(OBn)-Cys-Trp-Gly-NHNH$_2$ Seq ID No: 43;
Cbz-His-Tyr(OBn)-Cys-Trp-Gly-OMe Seq ID No: 44; and
Cbz-His-Tyr(OBn)-Cys-Trp-Gly Seq ID No: 45,
in admixture with a pharmaceutically acceptable excipient, diluent, or carrier.

28. A method of treating ras-related cancer comprising administering to a mammal suffering therefrom a therapeutically effective amount of a compound selected from the group consisting of Cbz-His-Tyr(OBn)-Cys-Trp-D-Ala-NH$_2$;
Cbz-His-Tyr(OBn)-Cys-Trp-D-Ala-NHMe;
Cbz-His-Tyr(OBn)-Cys-Trp-D-Ala-NHEt;
Cbz-His-Tyr(OBn)-Cys-Trp-D-Ala-NHNH$_2$;
Cbz-His-Tyr(OBn)-Cys-Trp-D-Ala-OMe;
Cbz-His-Tyr(OBn)-Cys-Trp-D-Ala;
Cbz-His-Tyr(OBn)-Cys-Trp-Ala-NH$_2$ Seq ID No: 34;
Cbz-His-Tyr(OBn)-Cys-Trp-Ala-NHMe Seq ID No: 35;
Cbz-His-Tyr(OBn)-Cys-Trp-Ala-NHEt Seq ID No: 36;
Cbz-His-Tyr(OBn)-Cys-Trp-Ala-NHNH$_2$ Seq ID No: 37;

Cbz-His-Tyr(OBn)-Cys-Trp-Ala-OMe Seq ID No: 38;
Cbz-His-Tyr(OBn)-Cys-Trp-Ala Seq ID No: 39;
Cbz-His-Tyr(OBn)-Cys-Trp-Gly-NH$_2$ Seq ID No: 40;
Cbz-His-Tyr(OBn)-Cys-Trp-Gly-NHMe Seq ID No: 41;
Cbz-His-Tyr(OBn)-Cys-Trp-Gly-NHEt Seq ID No: 42;
Cbz-His-Tyr(OBn)-Cys-Trp-Gly-NHNH$_2$ Seq ID No: 43;
Cbz-His-Tyr(OBn)-Cys-Trp-Gly-OMe Seq ID No: 44; and
Cbz-His-Tyr(OBn)-Cys-Trp-Gly Seq ID No: 45.

* * * * *